(12) United States Patent
Shanjani et al.

(10) Patent No.: US 10,383,705 B2
(45) Date of Patent: Aug. 20, 2019

(54) ORTHODONTIC APPLIANCE PERFORMANCE MONITOR

(71) Applicant: Align Technology, Inc., San Jose, CA (US)

(72) Inventors: Yaser Shanjani, Sunnyvale, CA (US); Bruce Cam, San Jose, CA (US); Allen R. Boronkay, San Jose, CA (US); Jun Sato, San Jose, CA (US); John Y. Morton, San Jose, CA (US); Chunhua Li, Cupertino, CA (US); Srinivas Kaza, Mountain View, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 15/625,850

(22) Filed: Jun. 16, 2017

(65) Prior Publication Data
US 2018/0000565 A1    Jan. 4, 2018

Related U.S. Application Data

(60) Provisional application No. 62/351,408, filed on Jun. 17, 2016.

(51) Int. Cl.
*A61C 7/08*    (2006.01)
*A61C 7/00*    (2006.01)
*A61C 19/04*   (2006.01)

(52) U.S. Cl.
CPC .............. *A61C 7/08* (2013.01); *A61C 7/002* (2013.01); *A61C 19/04* (2013.01)

(58) Field of Classification Search
CPC .. A61C 7/08; A61C 7/002; A61C 7/00; A61C 7/14; A61C 7/16; A61C 19/04;
(Continued)

(56) References Cited

U.S. PATENT DOCUMENTS

| 2,171,695 A | 9/1939 | Harper |
| 2,467,432 A | 4/1949 | Kesling |
(Continued)

FOREIGN PATENT DOCUMENTS

| AU | 517102 B | 11/1977 |
| AU | 3031677 A | 11/1977 |
(Continued)

OTHER PUBLICATIONS

US 8,553,966 B1, 10/2013, Alpern et al. (withdrawn)
(Continued)

*Primary Examiner* — Wade Miles
*Assistant Examiner* — Shannel N Wright
(74) *Attorney, Agent, or Firm* — Shay Glenn LLP

(57) ABSTRACT

Apparatuses and methods for monitoring the performance of an orthodontic appliance for repositioning a patient's teeth. An orthodontic appliance may include a plurality of teeth receiving cavities shaped to reposition the patient's teeth from an initial arrangement towards a target arrangement, and one or more sensors configured to determine tooth movement (based on position and/or orientation) and/or forces applied to the teeth. The sensor may be distributed between attachments and aligners that mate with the attachments.

27 Claims, 20 Drawing Sheets

(58) Field of Classification Search
CPC .............. A61C 19/05; A61C 2204/005; A61C 2204/002; A61B 5/682; A61B 5/228; A61B 5/4557; A61B 5/1111; A61F 5/56; A61F 5/566; A61F 2005/563
See application file for complete search history.

(56) References Cited

U.S. PATENT DOCUMENTS

| | | |
|---|---|---|
| 2,531,222 A | 11/1950 | Kesling |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,134,203 A | 1/1979 | Pearlman |
| 4,195,046 A | 3/1980 | Kesling |
| 4,253,828 A | 3/1981 | Coles et al. |
| 4,255,138 A | 3/1981 | Frohn |
| 4,324,546 A | 4/1982 | Heitlinger et al. |
| 4,324,547 A | 4/1982 | Arcan et al. |
| 4,348,178 A | 9/1982 | Kurz |
| 4,419,992 A | 12/1983 | Chorbajian |
| 4,433,956 A | 2/1984 | Witzig |
| 4,478,580 A | 10/1984 | Barrut |
| 4,500,294 A | 2/1985 | Lewis |
| 4,505,673 A | 3/1985 | Yoshii |
| 4,519,386 A | 5/1985 | Sullivan |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,629,424 A | 12/1986 | Lauks et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,037,295 A | 8/1991 | Bergersen |
| 5,055,039 A | 10/1991 | Abbatte et al. |
| 5,100,316 A | 3/1992 | Wildman |
| 5,103,838 A | 4/1992 | Yousif |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,204,670 A | 4/1993 | Stinton |
| 5,242,304 A | 9/1993 | Truax et al. |
| 5,245,592 A | 9/1993 | Kuemmel et al. |
| 5,273,429 A | 12/1993 | Rekow et al. |
| 5,278,756 A | 1/1994 | Lemchen et al. |
| 5,306,144 A | 4/1994 | Hibst et al. |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,499,633 A | 3/1996 | Fenton |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,725,376 A | 3/1998 | Poirier |
| 5,725,378 A | 3/1998 | Wang |
| 5,730,151 A * | 3/1998 | Summer ............... A61C 19/04 600/587 |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |

(56) References Cited

U.S. PATENT DOCUMENTS

| | | |
|---|---|---|
| 5,800,174 A | 9/1998 | Andersson |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,904,479 A | 5/1999 | Staples |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,980,246 A | 11/1999 | Ramsay et al. |
| 5,989,023 A | 11/1999 | Summer et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,099,303 A | 8/2000 | Gibbs et al. |
| 6,099,314 A | 8/2000 | Kopelman et al. |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,212,435 B1 | 4/2001 | Lattner et al. |
| 6,217,334 B1 | 4/2001 | Hultgren |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,299,438 B1 | 10/2001 | Sahagian et al. |
| 6,309,215 B1 | 10/2001 | Phan et al. |
| 6,315,553 B1 | 11/2001 | Sachdeva et al. |
| 6,328,745 B1 | 12/2001 | Ascherman |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,402,510 B1 | 6/2002 | Williams |
| 6,402,707 B1 | 6/2002 | Ernst |
| 6,405,729 B1 | 6/2002 | Thornton |
| 6,413,086 B1 | 7/2002 | Womack |
| 6,436,058 B1 | 8/2002 | Krahner et al. |
| 6,450,167 B1 | 9/2002 | David et al. |
| 6,450,807 B1 | 9/2002 | Chishti et al. |
| 6,482,298 B1 | 11/2002 | Bhatnagar |
| 6,499,995 B1 | 12/2002 | Schwartz |
| 6,515,593 B1 | 2/2003 | Stark et al. |
| 6,516,805 B1 | 2/2003 | Thornton |
| 6,520,772 B2 | 2/2003 | Williams |
| 6,524,101 B1 | 2/2003 | Phan et al. |
| 6,540,707 B1 | 4/2003 | Stark et al. |
| 6,572,372 B1 | 6/2003 | Phan et al. |
| 6,573,998 B2 | 6/2003 | Cohen Sabban |
| 6,594,539 B1 | 7/2003 | Geng |
| 6,597,934 B1 | 7/2003 | de Jong et al. |
| 6,602,070 B2 | 8/2003 | Miller et al. |
| 6,611,783 B2 | 8/2003 | Kelly et al. |
| 6,613,001 B1 | 9/2003 | Dworkin |
| 6,616,579 B1 | 9/2003 | Reinbold et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,640,128 B2 | 10/2003 | Vilsmeier et al. |
| 6,697,164 B1 | 2/2004 | Babayoff et al. |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,749,414 B1 | 6/2004 | Hanson et al. |
| 6,830,450 B2 | 12/2004 | Knopp et al. |
| 6,832,912 B2 | 12/2004 | Mao |
| 6,885,464 B1 | 4/2005 | Pfeiffer et al. |
| 6,890,285 B2 | 5/2005 | Rahman et al. |
| 6,976,841 B1 | 12/2005 | Osterwalder |
| 7,036,514 B2 | 5/2006 | Heck |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,138,640 B1 | 11/2006 | Delgado et al. |
| 7,142,312 B2 | 11/2006 | Quadling et al. |
| 7,166,063 B2 | 1/2007 | Rahman et al. |
| 7,184,150 B2 | 2/2007 | Quadling et al. |
| 7,192,273 B2 | 3/2007 | McSurdy |
| 7,220,124 B2 | 5/2007 | Taub et al. |
| 7,286,954 B2 | 10/2007 | Kopelman et al. |
| 7,292,759 B2 | 11/2007 | Boutoussov et al. |
| 7,302,842 B2 | 12/2007 | Biester et al. |
| 7,338,327 B2 | 3/2008 | Sticker et al. |
| D565,509 S | 4/2008 | Fechner et al. |
| 7,351,116 B2 | 4/2008 | Dold |
| 7,357,637 B2 | 4/2008 | Liechtung |
| 7,450,231 B2 | 11/2008 | Johs et al. |
| 7,458,810 B2 | 12/2008 | Bergersen |
| 7,460,230 B2 | 12/2008 | Johs et al. |
| 7,462,076 B2 | 12/2008 | Walter et al. |
| 7,463,929 B2 | 12/2008 | Simmons |
| 7,500,851 B2 | 3/2009 | Williams |
| D594,413 S | 6/2009 | Palka et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,724,378 B2 | 5/2010 | Babayoff |
| D618,619 S | 6/2010 | Walter |
| 7,731,508 B2 | 6/2010 | Borst |
| 7,735,217 B2 | 6/2010 | Borst |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,872,760 B2 | 1/2011 | Ertl |
| 7,874,836 B2 | 1/2011 | McSurdy |
| 7,874,849 B2 | 1/2011 | Sticker et al. |
| 7,878,801 B2 | 2/2011 | Abolfathi et al. |
| 7,892,474 B2 | 2/2011 | Shkolnik et al. |
| 7,907,280 B2 | 3/2011 | Johs et al. |
| 7,929,151 B2 | 4/2011 | Liang et al. |
| 7,947,508 B2 | 5/2011 | Tricca et al. |
| 7,959,308 B2 | 6/2011 | Freeman et al. |
| 7,963,766 B2 | 6/2011 | Cronauer |
| 7,986,415 B2 | 7/2011 | Thiel et al. |
| 8,017,891 B2 | 9/2011 | Nevin |
| 8,026,916 B2 | 9/2011 | Wen |
| 8,027,709 B2 | 9/2011 | Arnone et al. |
| 8,038,444 B2 | 10/2011 | Kitching et al. |

(56) References Cited

U.S. PATENT DOCUMENTS

| | | | |
|---|---|---|---|
| 8,054,556 B2 | 11/2011 | Chen et al. |
| 8,070,490 B1 | 12/2011 | Roetzer et al. |
| 8,077,949 B2 | 12/2011 | Liang et al. |
| 8,083,556 B2 | 12/2011 | Stadler et al. |
| D652,799 S | 1/2012 | Mueller |
| 8,118,592 B2 | 2/2012 | Tortorici |
| 8,126,025 B2 | 2/2012 | Takeda |
| 8,144,954 B2 | 3/2012 | Quadling et al. |
| 8,160,334 B2 | 4/2012 | Thiel et al. |
| 8,201,560 B2 | 6/2012 | Dembro |
| 8,215,312 B2 | 7/2012 | Garabadian et al. |
| 8,240,018 B2 | 8/2012 | Walter et al. |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,520,922 B2 | 8/2013 | Wang et al. |
| 8,520,925 B2 | 8/2013 | Duret et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,743,923 B2 | 6/2014 | Geske et al. |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,870,566 B2 | 10/2014 | Bergersen |
| 8,878,905 B2 | 11/2014 | Fisker et al. |
| 8,899,976 B2 | 12/2014 | Chen et al. |
| 8,936,463 B2 | 1/2015 | Mason et al. |
| 8,948,482 B2 | 2/2015 | Levin |
| 8,956,058 B2 | 2/2015 | Rösch |
| 8,992,216 B2 | 3/2015 | Karazivan |
| 9,022,792 B2 | 5/2015 | Sticker et al. |
| 9,039,418 B1 | 5/2015 | Rubbert |
| 9,084,535 B2 | 7/2015 | Girkin et al. |
| 9,108,338 B2 | 8/2015 | Sirovskiy et al. |
| 9,144,512 B2 | 9/2015 | Wagner |
| 9,192,305 B2 | 11/2015 | Levin |
| 9,204,952 B2 | 12/2015 | Lampalzer |
| 9,242,118 B2 | 1/2016 | Brawn |
| 9,261,358 B2 | 2/2016 | Atiya et al. |
| 9,336,336 B2 | 5/2016 | Deichmann et al. |
| 9,351,810 B2 | 5/2016 | Moon |
| 9,375,300 B2 | 6/2016 | Matov et al. |
| 9,408,743 B1 | 8/2016 | Wagner |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,500,635 B2 | 11/2016 | Islam |
| 9,506,808 B2 | 11/2016 | Jeon et al. |
| 9,545,331 B2 | 1/2017 | Ingemarsson-Matzen |
| 9,584,771 B2 | 2/2017 | Mandelis et al. |
| 9,675,430 B2 | 6/2017 | Verker et al. |
| 9,693,839 B2 | 7/2017 | Atiya et al. |
| 9,744,006 B2 | 8/2017 | Ross |
| 9,861,451 B1 | 1/2018 | Davis |
| 9,936,186 B2 | 4/2018 | Jesenko et al. |
| 10,159,541 B2 | 12/2018 | Bindayel |
| 2001/0038705 A1 | 11/2001 | Rubbert et al. |
| 2002/0010568 A1 | 1/2002 | Rubbert et al. |
| 2002/0015934 A1 | 2/2002 | Rubbert et al. |
| 2003/0009252 A1 | 1/2003 | Pavlovskaia et al. |
| 2003/0035061 A1 | 2/2003 | Iwaki et al. |
| 2003/0049581 A1 | 3/2003 | Deluke |
| 2003/0139834 A1 | 7/2003 | Nikolskiy et al. |
| 2003/0190575 A1 | 10/2003 | Hilliard |
| 2003/0207224 A1 | 11/2003 | Lotte |
| 2003/0224311 A1 | 12/2003 | Cronauer |
| 2004/0009449 A1 | 1/2004 | Mah et al. |
| 2004/0019262 A1 | 1/2004 | Perelgut |
| 2004/0058295 A1 | 3/2004 | Bergersen |
| 2004/0094165 A1 | 5/2004 | Cook |
| 2004/0158194 A1 | 8/2004 | Wolff et al. |
| 2004/0167646 A1 | 8/2004 | Jelonek et al. |
| 2004/0229185 A1 | 11/2004 | Knopp |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0048433 A1 | 3/2005 | Hilliard |
| 2005/0100333 A1 | 5/2005 | Kerschbaumer et al. |
| 2005/0181333 A1 | 8/2005 | Karazivan et al. |
| 2005/0186524 A1 | 8/2005 | Abolfathi et al. |
| 2005/0244781 A1 | 11/2005 | Abels et al. |
| 2006/0084024 A1 | 4/2006 | Farrell |
| 2006/0099546 A1 | 5/2006 | Bergersen |
| 2006/0154198 A1 | 7/2006 | Durbin et al. |
| 2006/0166157 A1* | 7/2006 | Rahman ............... A61B 5/4833 |
| | | | 433/6 |
| 2006/0223032 A1 | 10/2006 | Fried et al. |
| 2006/0223342 A1 | 10/2006 | Borst et al. |
| 2006/0234179 A1 | 10/2006 | Wen et al. |
| 2007/0046865 A1 | 3/2007 | Umeda et al. |
| 2007/0053048 A1 | 3/2007 | Kumar et al. |
| 2007/0087300 A1 | 4/2007 | Willison et al. |
| 2007/0106138 A1 | 5/2007 | Beiski et al. |
| 2007/0184402 A1 | 8/2007 | Boutoussov et al. |
| 2007/0231765 A1 | 10/2007 | Phan et al. |
| 2007/0238065 A1 | 10/2007 | Sherwood et al. |
| 2008/0045053 A1 | 2/2008 | Stadler et al. |
| 2008/0057461 A1 | 3/2008 | Cheng et al. |
| 2008/0090208 A1 | 4/2008 | Rubbert |
| 2008/0115791 A1 | 5/2008 | Heine |
| 2008/0118886 A1 | 5/2008 | Liang et al. |
| 2008/0169122 A1 | 7/2008 | Shiraishi et al. |
| 2008/0176448 A1 | 7/2008 | Muller et al. |
| 2008/0242144 A1 | 10/2008 | Dietz |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kaneko et al. |
| 2009/0087050 A1 | 4/2009 | Gandyra |
| 2009/0105523 A1* | 4/2009 | Kassayan ................ A61C 7/00 |
| | | | 600/25 |
| 2009/0130620 A1 | 5/2009 | Yazdi et al. |
| 2009/0170050 A1 | 7/2009 | Marcus |
| 2009/0210032 A1 | 8/2009 | Beiski et al. |
| 2009/0218514 A1 | 9/2009 | Klunder et al. |
| 2009/0246726 A1 | 10/2009 | Chelnokov et al. |
| 2009/0281433 A1* | 11/2009 | Saadat ............... A61M 5/14244 |
| | | | 600/483 |
| 2009/0286195 A1* | 11/2009 | Sears .................... A61C 7/14 |
| | | | 433/8 |
| 2009/0298017 A1 | 12/2009 | Boerjes et al. |
| 2009/0305540 A1 | 12/2009 | Stadler et al. |
| 2009/0317757 A1* | 12/2009 | Lemchen ................ A61C 7/14 |
| | | | 433/24 |
| 2010/0015565 A1 | 1/2010 | Carrillo et al. |
| 2010/0019170 A1 | 1/2010 | Hart et al. |
| 2010/0045902 A1 | 2/2010 | Ikeda et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0231577 A1 | 9/2010 | Kim et al. |
| 2010/0312484 A1 | 12/2010 | DuHamel et al. |
| 2011/0007920 A1* | 1/2011 | Abolfathi ............. H04R 25/606 |
| | | | 381/326 |
| 2011/0012901 A1 | 1/2011 | Kaplanyan |

(56) References Cited

U.S. PATENT DOCUMENTS

| | | |
|---|---|---|
| 2011/0045428 A1 | 2/2011 | Boltunov et al. |
| 2011/0065060 A1 | 3/2011 | Teixeira et al. |
| 2011/0081625 A1 | 4/2011 | Fuh |
| 2011/0102549 A1 | 5/2011 | Takahashi |
| 2011/0102566 A1 | 5/2011 | Zakian et al. |
| 2011/0136090 A1 | 6/2011 | Kazemi |
| 2011/0143300 A1 | 6/2011 | Villaalba |
| 2011/0143673 A1 | 6/2011 | Landesman et al. |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0129117 A1 | 5/2012 | McCance |
| 2012/0147912 A1 | 6/2012 | Moench et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0122027 A1 | 5/2014 | Andreiko et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0363778 A1 | 12/2014 | Parker |
| 2015/0002649 A1 | 1/2015 | Nowak et al. |
| 2015/0079531 A1 | 3/2015 | Heine |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0140502 A1 | 5/2015 | Brawn et al. |
| 2015/0164335 A1 | 6/2015 | Van Der Poel et al. |
| 2015/0173856 A1 | 6/2015 | Iowe et al. |
| 2015/0230885 A1 | 8/2015 | Wucher |
| 2015/0238280 A1 | 8/2015 | Wu et al. |
| 2015/0238282 A1* | 8/2015 | Kuo ............... A61C 7/002 433/6 |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0325044 A1 | 11/2015 | Lebovitz |
| 2015/0338209 A1 | 11/2015 | Knüttel |
| 2015/0374469 A1* | 12/2015 | Konno ............. A61B 5/228 433/27 |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0328843 A1 | 11/2016 | Graham et al. |
| 2016/0367188 A1 | 12/2016 | Malik et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0049311 A1 | 2/2017 | Borovinskih et al. |
| 2017/0049326 A1 | 2/2017 | Alfano et al. |
| 2017/0056131 A1* | 3/2017 | Alauddin ............... A61B 5/742 |
| 2017/0086943 A1 | 3/2017 | Mah |
| 2017/0100214 A1 | 4/2017 | Wen |
| 2017/0156821 A1 | 6/2017 | Kopelman et al. |
| 2017/0215739 A1 | 8/2017 | Miyasato |
| 2017/0265970 A1 | 9/2017 | Verker |
| 2017/0319054 A1 | 11/2017 | Miller et al. |
| 2017/0325690 A1 | 11/2017 | Salah et al. |
| 2017/0340411 A1 | 11/2017 | Akselrod |
| 2018/0000563 A1 | 1/2018 | Shanjani et al. |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1* | 3/2018 | Ha ........................ A61C 7/006 |
| 2018/0085059 A1* | 3/2018 | Lee ........................ A61B 5/682 |
| 2018/0353264 A1 | 12/2018 | Riley et al. |
| 2018/0360567 A1 | 12/2018 | Xue et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0029522 A1 | 1/2019 | Sato et al. |
| 2019/0029784 A1 | 1/2019 | Moalem et al. |

FOREIGN PATENT DOCUMENTS

| | | |
|---|---|---|
| AU | 5598894 A | 6/1994 |
| CA | 1121955 A1 | 4/1982 |
| CN | 1655732 A | 8/2005 |
| CN | 1655733 A | 8/2005 |
| CN | 102017658 A | 4/2011 |
| CN | 103889364 A | 6/2014 |
| CN | 105997274 A | 10/2016 |
| DE | 2749802 A1 | 5/1978 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2930334 A1 | 10/2009 |
| GB | 1550777 A | 8/1979 |
| JP | 53-058191 A | 5/1978 |
| JP | 4028359 A | 1/1992 |

(56) References Cited

FOREIGN PATENT DOCUMENTS

| | | |
|---|---|---|
| JP | 08-508174 A | 9/1996 |
| JP | 2007260158 A | 10/2007 |
| JP | 2007537824 A | 12/2007 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009205330 A | 9/2009 |
| JP | 2010017726 A | 1/2010 |
| JP | 2011087733 A | 5/2011 |
| JP | 2013007645 A | 1/2013 |
| JP | 201735173 A | 2/2017 |
| KR | 10-1266966 B1 | 5/2013 |
| KR | 10-2016-041632 A | 4/2016 |
| KR | 10-2016-0071127 A | 6/2016 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | WO02/017776 A2 | 3/2002 |
| WO | WO02/062252 A1 | 8/2002 |
| WO | WO02/095475 A1 | 11/2002 |
| WO | WO03/003932 A2 | 1/2003 |
| WO | WO2006/096558 A2 | 9/2006 |
| WO | WO2006/133548 A1 | 12/2006 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/123892 A2 | 10/2010 |
| WO | WO2012/007003 A1 | 1/2012 |
| WO | WO2012/064684 A2 | 5/2012 |
| WO | WO-2012064684 A2 * 5/2012 .......... A61B 5/4833 |  |
| WO | WO2012/074304 A2 | 6/2012 |
| WO | WO2012/078980 A2 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |
| WO | WO-2016116874 A1 * 7/2016 ............ A61C 7/002 |  |
| WO | WO2016/200177 A1 | 12/2016 |
| WO | WO2017/006176 A1 | 1/2017 |
| WO | WO2017/182654 A1 | 10/2017 |
| WO | WO2018/085718 A2 | 5/2018 |
| WO | WO2019/018784 A1 | 1/2019 |

OTHER PUBLICATIONS

Begole et al.; A Computer System for the Analysis of Dental Casts; The Angle Orthodontist; 51(3); pp. 252-258; Jul. 1981.

Biggerstaff; Computerized Diagnostic Setups and Simulations; Angle Orthodontist; 40(I); pp. 28-36; Jan. 1970.

Blu et al.; Linear interpolation revitalized; IEEE Transactions on Image Processing; 13(5); pp. 710-719; May 2004.

Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.

Gao et al.; 3-D element Generation for Multi-Connected Complex Dental and Mandibular Structure; IEEE Proceedings International Workshop in Medical Imaging and Augmented reality; pp. 267-271; Jun. 12, 2001.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Kochanek; Interpolating Splines with Local Tension, Continuity and Bias Control; Computer Graphics; 18(3); pp. 33-41; Jan. 1, 1984.

Kunii et al.; Articulation Simulation for an Intelligent Dental Care System; Displays; 15(3); pp. 181-188; Jul. 1994.

Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.

Richmond et al.; The Development of the PAR Index (Peer Assessment Rating): Reliability and Validity.; The European Journal of Orthodontics; 14(2); pp. 125-139; Apr. 1992.

Sturman; Interactive Keyframe Animation of 3-D Articulated Models; Proceedings Graphics Interface '84; vol. 86; pp. 35-40; May-Jun. 1984.

Van Der Linden; A New Method to Determine Tooth Positions and Dental Arch Dimensions; Journal of Dental Research; 51(4); p. 1104; Jul.-Aug. 1972.

Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.

Verstreken et al.; An Image-Guided Planning System for Endosseous Oral Implants; IEEE Transactions on Medical Imaging; 17(5); pp. 842-852; Oct. 1998.

Williams; Dentistry and CAD/CAM: Another French Revolution; J. Dent. Practice Admin.; 4(1); pp. 2-5 Jan./Mar. 1987.

Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.

Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.

Cramer; U.S. Appl. No. 15/937,569 entitled "Apparatuses and methods assisting in dental therapies," filed Mar. 27, 2018.

Cramer et al.; U.S. Appl. No. 15/942,341 entitled "Orthodontic appliances including at least partially un-erupted teeth and method of forming them," filed Mar. 30, 2018.

AADR. American Association for Dental Research; Summary of Activities; Los Angeles, CA; p. 195; Mar. 20-23,(year of pub. sufficiently earlier than effective US filing date and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Allesee Orthodontic Appliance: Important Tip About Wearing the Red White & Blue Active Clear Retainer System; Allesee Orthodontic Appliances-Pro Lab; 1 page; (year of pub. sufficiently earlier than effective US filing date and any foreign priority date); 1998.

Allesee Orthodontic Appliances: DuraClearTM; Porduct information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product

(56) References Cited

OTHER PUBLICATIONS information for doctors); retrieved from the internet (http://ormco.com/aoa/appliancesservices/RWB/doctorhtml); 5 pages on May 19, 2003.
Allesee Orthodontic Appliances; The Choice Is Clear: Red, White & Blue . . . The Simple, Affordable, No-Braces Treatment; p(roduct information), 6 pages; (year of pub. sufficiently earlier than effective US filing date and any foreign priority date) 2003.
Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.
Allesee Orthodontic Appliances; The Red, White & Blue Way to Improve Your Smile; (information for patients), 2 pages; (year of pub. sufficiently earlier than effective US filing date and any foreign priority date) 1992.
Allesee Orthodontic Appliances; You may be a candidate for this invisible no-braces treatment; product information for patients; 2 pages; (year of pub. sufficiently earlier than effective US filing date and any foreign priority date) 2002.
Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.
Altschuler et al.; Laser Electro-Optic System for Rapid Three-Dimensional (3D) Topographic Mapping of Surfaces; Optical Engineering; 20(6); pp. 953-961; Dec. 1981.
Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.
Altschuler; 3D Mapping of Maxillo-Facial Prosthesis; AADR Abstract #607; 2 pages total, (year of pub. sufficiently earlier than effective US filing date and any foreign priority date) 1980.
Andersson et al.; Clinical Results with Titanium Crowns Fabricated with Machine Duplication and Spark Erosion; Acta Odontologica Scandinavica; 47(5); pp. 279-286; Oct. 1989.
Andrews, The Six Keys to Optimal Occlusion Straight Wire, Chapter 3, L.A. Wells; pp. 13-24; (year of pub. sufficiently earlier than effective US filing date and any foreign priority date) 1989.
Barone et al.; Creation of 3D multi-body orthodontic models by using independent imaging sensors; Sensors; 13(2); pp. 2033-2050; Feb. 5, 2013.
Bartels et al.; An Introduction to Splines for Use in Computer Graphics and Geometric Modeling; Morgan Kaufmann Publishers; pp. 422-425 Jan. 1, 1987.
Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.
Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.
Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.
Baumrind; Integrated Three-Dimensional Craniofacial Mapping: Background, Principles, and Perspectives; Seminars in Orthodontics; 7(4); pp. 223-232; Dec. 2001.
Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.
Bhatia et al.; A Computer-Aided Design for Orthognathic Surgery; British Journal of Oral and Maxillofacial Surgery; 22(4); pp. 237-253; Aug. 1, 1984.
Biggerstaff et al.; Computerized Analysis of Occlusion in the Postcanine Dentition; American Journal of Orthodontics; 61(3); pp. 245-254; Mar. 1972.
Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Bourke, Coordinate System Transformation; 1 page; retrived from the internet (http://astronomy.swin.edu.au/' pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford; Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
DCS Dental AG; The CAD/CAM 'DCS Titan System' for Production of Crowns/Bridges; DSC Production; pp. 1-7; Jan. 1992.

(56) References Cited

OTHER PUBLICATIONS

Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dent-X; Dentsim...Dent-x's virtual reality 3-D training simulator...A revolution in dental education; 6 pages; retrieved from the internet (http://www.dent-x.com/DentSim.htm); on Sep. 24, 1998.
Doyle; Digital Dentistry; Computer Graphics World; pp. 50-52 andp. 54; Oct. 2000.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.
Faber et al.; Computerized Interactive Orthodontic Treatment Planning; American Journal of Orthodontics; 73(1); pp. 36-46; Jan. 1978.
Felton et al.; A Computerized Analysis of the Shape and Stability of Mandibular Arch Form; American Journal of Orthodontics and Dentofacial Orthopedics; 92(6); pp. 478-483; Dec. 1987.
Friede et al.; Accuracy of Cephalometric Prediction in Orthognathic Surgery; Journal of Oral and Maxillofacial Surgery; 45(9); pp. 754-760; Sep. 1987.
Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.
Gim-Alldent Deutschland, "Das DUX System: Die Technik," 3 pages; (English Translation Included); (year of pub. sufficiently earlier than effective US filing date and any foreign priority date); 2002.
Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982 &Month=06&ArticleNum+); 21 pages; Jun. 1982.
Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.
Guess et al.; Computer Treatment Estimates in Orthodontics and Orthognathic Surgery; Journal of Clinical Orthodontics; 23(4); pp. 262-268; 11 pages; (Author Manuscript); Apr. 1989.
Heaven et al.; Computer-Based Image Analysis of Artificial Root Surface Caries; Abstracts of Papers #2094; Journal of Dental Research; 70:528; (Abstract Only); Apr. 17-21, 1991.
Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa..); on Nov. 5, 2004.
Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Inclused); Feb. 1987.
Hoffmann et al.; Role of Cephalometry for Planning of Jaw Orthopedics and Jaw Surgery Procedures; Informatbnen, pp. 375-396; (English Abstract Included); Mar. 1991.
Hojjatie et al.; Three-Dimensional Finite Element Analysis of Glass-Ceramic Dental Crowns; Journal of Biomechanics; 23(11); pp. 1157-1166; Jan. 1990.
Huckins; CAD-CAM Generated Mandibular Model Prototype from MRI Data; AAOMS, p. 96; (Abstract Only); (year of pub. sufficiently earlier than effective US filing date and any foreign priority date) 1999.
JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Moermann et al, Computer Machined Adhesive Porcelain Inlays: Margin Adaptation after Fatigue Stress; IADR Abstract 339; J. Dent. Res.; 66(a);763; (Abstract Only); (year of pub. sufficiently earlier than effective US filing date and any foreign priority date) 1987.
Moles; Correcting Mild Malalignments—As Easy as One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Macine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.

(56) References Cited

OTHER PUBLICATIONS

Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages , Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thorlabs; Pellin broca prisms; 1 page; retrieved from the Internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-8; Sep.-Oct. 1992.
TRU-TATN Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Van Der Linden et al.; Three-Dimensional Analysis of Dental Casts by Means of the Optocom; Journal of Dental Research; 51(4); p. 1100; Jul.-Aug. 1972.
Van Hilsen et al.; Comparing potential early caries assessment methods for teledentistry; BMC Oral Health; 13(16); doi: 10.1186/1472-6831-13-16; 9 pages; Mar. 2013.
Varady et al.; Reverse Engineering of Geometric Models' An Introduction; Computer-Aided Design; 29(4); pp. 255-268; 20 pages; (Author Manuscript); Apr. 1997.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23 (10); pp. 694-700; Oct. 1989.
Wells; Application of the Positioner Appliance in Orthodontic Treatment; American Journal of Orthodontics; 58(4); pp. 351-366; Oct. 1970.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment

(56) References Cited

OTHER PUBLICATIONS

Planning and Imaging Processing; Symposium: Computerized Facial Imaging in Oral and Maxilofacial Surgery; p. 5; Presented on Sep. 13, 1990.
WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.
Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.
Alves et al.; New trends in food allergens detection: toward biosensing strategies; Critical Reviews in Food Science and Nutrition; 56(14); pp. 2304-2319; doi: 10.1080/10408398.2013.831026; Oct. 2016.
Arakawa et al; Mouthguard biosensor with telemetry system for monitoring of saliva glucose: A novel cavitas sensor; Biosensors and Bioelectronics; 84; pp. 106-111; Oct. 2016.
Bandodkar et al.; All-printed magnetically self-healing electrochemical devices; Science Advances; 2(11); 11 pages; e1601465; Nov. 2016.
Bandodkar et al.; Self-healing inks for autonomous repair of printable electrochemical devices; Advanced Electronic Materials; 1(12); 5 pages; 1500289; Dec. 2015.
Bandodkar et al.; Wearable biofuel cells: a review; Electroanalysis; 28(6); pp. 1188-1200; Jun. 2016.
Bandodkar et al.; Wearable chemical sensors: present challenges and future prospects; ACS Sensors; 1(5); pp. 464-482; May 11, 2016.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.
Di Muzio et al.; Minimum intensity projection (MinIP); 6 pages; retrieved from the internet (https://radiopaedia.org/articles/minimum-intensity-projection-minip) on Sep. 6, 2018.
Ellias et al.; Proteomic analysis of saliva identifies potential biomarkers for orthodontic tooth movement; The Scientific World Journal; vol. 2012; Article ID 647240; dio:10.1100/2012/647240; 7 pages; Jul. 2012.
Florez-Moreno; Time-related changes in salivary levels of the osteotropic factors sRANKL and OPG through orthodontic tooth movement; American Journal of Orthodontics and Dentofacial Orthopedics; 143 (1); pp. 92-100; Jan. 2013.
Imani et al.; A wearable chemical-electrophysiological hybrid biosensing system for real-time health and fitness monitoring; Nature Communications; 7; 11650. doi 1038/ncomms11650; 7 pages; May 23, 2016.
Jia et al.; Epidermal biofuel cells: energy harvesting from human perspiration; Angewandle Chemie International Edition; 52(28); pp. 7233-7236; Jul. 8, 2013.
Jia et al.; Wearable textile biofuel cells for powering electronics; Journal of Materials Chemistry A; 2(43); pp. 18184-18189; Oct. 14, 2014.
Jeerapan et al.; Stretchable biofuel cells as wearable textile-based self-powered sensors; Journal of Materials Chemistry A; 4(47); pp. 18342-18353; Dec. 21, 2016.
Kim et al.; Advanced materials for printed wearable electrochemical devices: A review; Advanced Electronic Materials; 3(1); 15 pages; 1600260; Jan. 2017.
Kim et al.; Noninvasive alcohol monitoring using a wearable tatto-based iontophoretic-biosensing system; ACS Sensors; 1(8); pp. 1011-1019; Jul. 22, 2016.
Kim et al.; Non-invasive mouthguard biosensor for continuous salivary monitoring of metabolites; Analyst; 139(7); pp. 1632-1636; Apr. 7, 2014.
Kim et al.; A wearable fingernail chemical sensing platform: pH sensing at your fingertips; Talanta; 150; pp. 622-628; Apr. 2016.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.
Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Parrilla et al.; A textile-based stretchable multi-ion potentiometric sensor; Advanced Healthcare Materials; 5(9); pp. 996-1001; May 2016.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Watson et al.; Pressures recorded at to denture base-mucosal surface interface in complete denture wearers; Journal of Oral Rehabilitation 14(6); pp. 575-589; Nov. 1987.
Windmiller et al.; Wearable electrochemical sensors and biosensors: a review; Electroanalysis; 25(1); pp. 29-46; Jan. 2013.
Wolf; Three-dimensional structure determination of semi-transparent objects from holographic data; Optics Communications; 1(4); pp. 153-156; Sep. 1969.
Zhou et al.; Bio-logic analysis of injury biomarker patterns in human serum samples; Talanta; 83(3); pp. 955-959; Jan. 15, 2011.
Zhou et al.; Biofuel cells for self-powered electrochemical biosensing and logic biosensing: A review; Electroanalysis; 24(2); pp. 197-209; Feb. 2012.
Nyukhtikov et al.; U.S. Appl. No. 15/998,883 entitled "Buccal corridor assessment and computation," filed Aug. 15, 2018.
Kopelman et al.; U.S. Appl. No. 16/152,281 entitled "Intraoral appliances for sampling soft-tissue," filed Oct. 4, 2018.
Morton et al.; U.S. Appl. No. 16/177,067 entitled "Dental appliance having selective occlusal loading and controlled intercuspation," filed Oct. 31, 2018.
Akopov et al.; U.S. Appl. No. 16/178,491 entitled "Automatic treatment planning," filed Nov. 1, 2018.
Elbaz et al.; U.S. Appl. No. 16/198,488 entitled "Intraoral scanner with dental diagnostics capabilities," filed Nov. 21, 2018.

(56) References Cited

OTHER PUBLICATIONS

Elbaz et al.; U.S. Appl. No. 16/188,262 entitled "Intraoral scanner with dental diagnostics capabilities," filed Nov. 12, 2018.
O'Leary et al.; U.S. Appl. No. 16/195,701 entitled "Orthodontic retainers," filed Nov. 19, 2018.
Shanjani et al., U.S. Appl. No. 16/206,894 entitled "Sensors for monitoring oral appliances," filed Nov. 28, 2019.
Shanjani et al., U.S. Appl. No. 16/231,906 entitled "Augmented reality enhancements for dental practitioners." Dec. 24, 2018.
Kopleman et al., U.S. Appl. No. 16/220,381 entitled "Closed loop adaptive orthodontic treatment methods and apparatuses," Dec. 14, 2018.
Sabina et al., U.S. Appl. No. 16/258,516 entitled "Diagnostic Introral Scanning" filed Jan. 25, 2019.
Yamada et al.; Simulation of fan-beam type optical computed-tomography imaging of strongly scattering and weakly absorbing media; Applied Optics; 32(25); pp. 4808-4814; Sep. 1, 1993.
Doruk et al.; The role of the headgear timer in extraoral co-operation; European Journal of Orthodontics; 26; pp. 289-291; Jun. 1, 2004.
Friedrich et al; Measuring system for in vivo recording of force systems in orthodontic treatment-concept and analysis of accuracy; J. Biomech.; 32(1); pp. 81-85; (Abstract Only) Jan. 1999.
Grest, Daniel; Marker-Free Human Motion Capture in Dynamic Cluttered Environments from a Single View-Point, PhD Thesis; 171 pages; Dec. 2007.
Invisalign; You were made to move. There's never been a better time to straighten your teeth with the most advanced clear aligner in the world; Product webpage; 2 pages; retrieved from the Internet (www.invisalign.com/) on Dec. 28, 2017.
Kumar et al.; Rapid maxillary expansion: A unique treatment modality in dentistry; J. Clin. Diagn. Res.; 5(4); pp. 906-911; Aug. 2011.
Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 19990.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Thera Mon; "Microsensor"; "2 pages"; retrieved from the interent (www.english.thera-mon.com/the-product/transponder/index.html); on Sep. 19, 2016.
Wikipedia; Palatal expansion; 3 pages; retrieved from the internet (https://en.wikipedia.org/wiki/Palatal_expansion) on Mar. 5, 2018.
Wireless Sensor Networks Magazine; Embedded Teeth for Oral Activity Recognition; 2 pages; retrievedon Sep. 19, 2016 from the internet (www.wsnmagazine.com/embedded-teeth/); Jul. 29, 2013.
Witt et al.; The wear-timing measuring device in orthodontics-cui bono? Reflections on the state-of-the-art in wear-timing measurement and compliance research in orthodontics; Fortschr Kieferorthop.; 52(3); pp. 117-125; (Translation Included) Jun. 1991.
Carrier et al.; U.S. Appl. No. 15/803,718 entitled "Methods and apparatuses for dental images," filed Nov. 3, 2017.
Kuo; U.S. Appl. No. 15/829,504 entitled "Dental appliance features for speech enhancement," filed Dec. 1, 2017.
Atiya et al.; U.S. Appl. No. 15/859,010 entitled "Compact confocal dental scanning apparatus," filed Dec. 29, 2017.
Shanjani et al.; U.S. Appl. No. 15/831,159 entitled "Palatal expanders and methods of expanding a palate," filed Dec. 4, 2017.
Wu et al.; U.S. Appl. No. 15/831,262 entitled "Methods and apparatuses for customizing a rapid palatal expander," filed Dec. 4, 2017.
Grove et al.; U.S. Appl. No. 15/726,243 entitled "Interproximal reduction templates," filed Oct. 5, 2017.
Video of DICOM to Surgical Guides; Can be viewed at <URL:https://youtu.be/47KtOmCEFQk; Published Apr. 4, 2016.
Sobral De Agular et al.; The gingival crevicular fluid as a source of biomarkers to enhance efficiency of orthodontic and functional treatment of growing patients; Bio. Med. Research International; vol. 2017; pp. 1-7; Article ID 3257235; (year of pub. sufficiently earlier than effective US filing date and any foreign priority date) 2017.

* cited by examiner

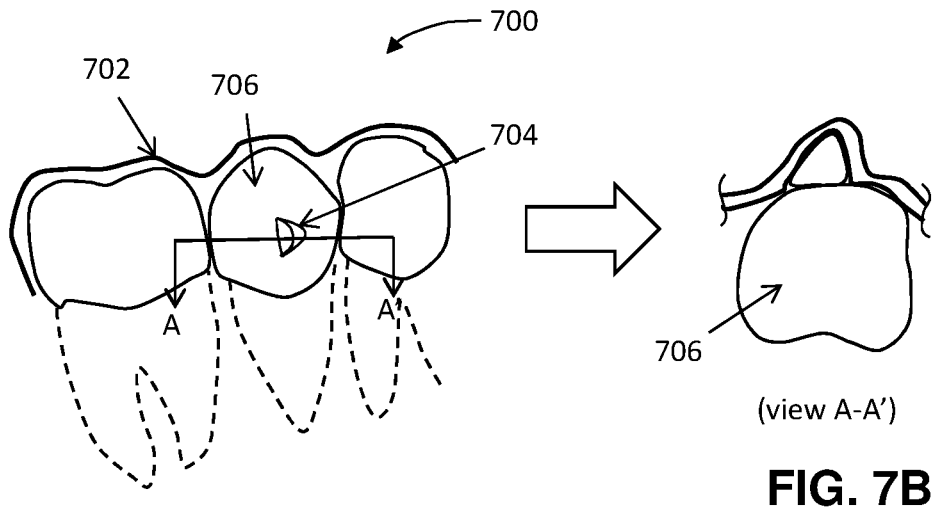
FIG. 7A
FIG. 7B
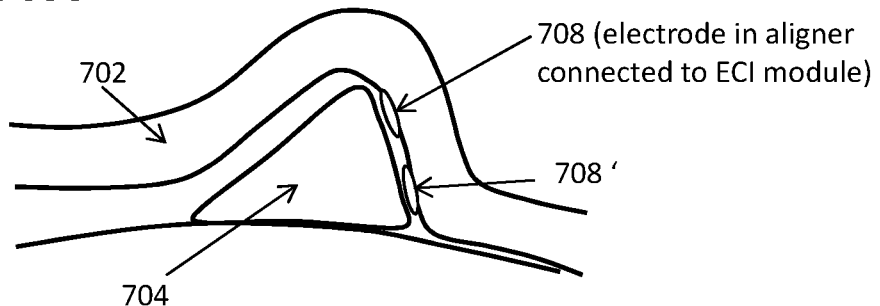
FIG. 7C
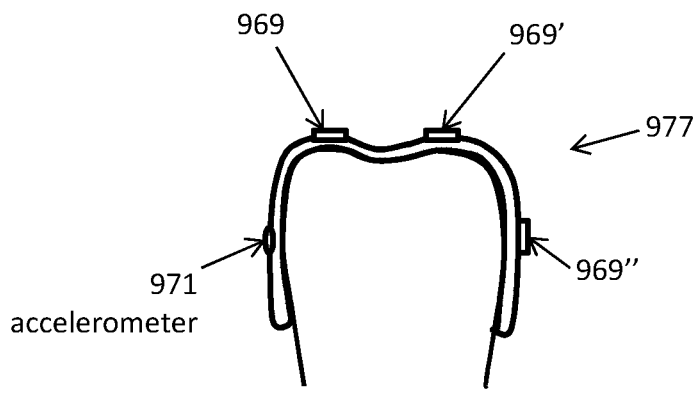
FIG. 7D

ORTHODONTIC APPLIANCE PERFORMANCE MONITOR

CROSS REFERENCE TO RELATED APPLICATIONS

This patent application claims priority to U.S. provisional patent application No. 62/351,408, field on Jun. 17, 2016, and is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

In some instances, the forces that are actually applied to a patient's teeth by an orthodontic appliance may differ from the intended forces for treating the teeth. Discrepancies between the planned and achieved repositioning forces may result in incomplete or undesirable tooth movements and deviations from the prescribed treatment plan. Accordingly, improved approaches for monitoring orthodontic appliance performance and treatment progress are needed.

SUMMARY OF THE DISCLOSURE

The present disclosure provides improved apparatuses (e.g., systems and devices) and methods for monitoring the performance of an orthodontic appliance for repositioning a patient's teeth. In some embodiments, the apparatuses described herein include one or more sensors configured to generate sensor data related to repositioning of the patient's teeth by an orthodontic appliance. For example, the data can be indicative of the amount of tooth movement achieved, the amount of force and/or pressure actually applied to the teeth by the appliance, or a combination thereof. As used herein, the term force may include linear force or angular/rotational forces, e.g., moment/torque (e.g., moment of force), or both. As used herein, deformations and displacements can be linear, angular, or both.

Advantageously, the embodiments described herein provide high value data that allows the practitioner to quantitatively assess whether the orthodontic appliance is repositioning the patient's teeth as planned. Optionally, the aligner performance data can be used as feedback to adjust the patient's treatment plan, also known as "adaptive closed-loop treatment," and can also inform the design and planning of future appliance-based orthodontic procedures.

For example, described herein are apparatuses for monitoring performance of an orthodontic appliance for repositioning a patient's teeth. The apparatus may include an orthodontic appliance comprising a plurality of teeth receiving cavities shaped to reposition the patient's teeth from an initial arrangement towards a target arrangement. Alternatively or additionally, the orthodontic apparatus may include brackets and wires for attachment to the teeth. The apparatus may include one or more sensors configured to generate sensor data related to the repositioning of the patient's teeth by the orthodontic appliance. The apparatus may also include a processor configured to process the sensor data in order to evaluate the performance of the orthodontic appliance in effecting the repositioning of the patient's teeth.

Any of the apparatuses described herein may include movement sensors. A movement sensor may also be referred to as a position sensor or a position/orientation sensors, because it may provide data indicating the relative position (e.g., two axis, such as x, y position, three axis, such as x, y, z position, etc.) or relative orientation (e.g., two angular orientations, such as pitch, yaw, or three angular orientations, such as pitch, roll, yaw, etc.). For example, described herein are orthodontic apparatuses for repositioning a patient's teeth and tracking tooth movement. These apparatuses may include: an aligner body comprising a plurality of teeth receiving cavities shaped to reposition the patient's teeth from an initial arrangement towards a target arrangement; a plurality of movement sensors coupled to the aligner body or configured to couple with the aligner body, wherein each movement sensor is configured to generate movement sensor data indicating one or more of: a position of the patient's tooth and an orientation of the patient's tooth; and a processor configured to receive and store the movement sensor data and to determine tooth movement from the movement sensor data.

Any of the apparatuses described herein may include both movement sensors (e.g., position/orientation sensors) and force sensors. For example, an orthodontic apparatus for repositioning a patient's teeth and tracking tooth movement may include: an aligner body comprising a plurality of teeth receiving cavities shaped to reposition the patient's teeth from an initial arrangement towards a target arrangement; a plurality of movement sensors coupled to the aligner body or on attachments (e.g., attachments) configured to couple the aligner body to the patient's teeth, wherein the plurality of movement sensors are each configured to generate movement sensor data indicating one or more of: a position of the patient's tooth and an orientation of the patient's tooth; a plurality of force sensors coupled to the aligner body or on attachments configured to couple the aligner body to the patient's teeth, wherein the plurality of force sensors are each configured to generate force sensor data indicating one or more of: an amount of force applied to the patient's teeth and a direction of force applied to the patient's teeth; and a processor configured to receive and store the movement sensor data and the force sensor data.

In any of the apparatuses described herein the apparatus may include movement sensors (e.g., position sensors) that include electromagnetic targets (e.g., magnets, coils, etc.) that may indicate position and/or orientation of a tooth when in the presence of an electromagnetic field. For example, an orthodontic apparatus for repositioning a patient's teeth and tracking tooth movement may include: one or more aligner bodies each comprising a plurality of teeth receiving cavities shaped to reposition the patient's teeth from an initial arrangement towards a target arrangement; a plurality of movement sensors coupled to the one or more aligner bodies or on attachments configured to couple the aligner body to the patient's teeth, wherein the plurality of movement sensors each comprise an electromagnetic target that is configured to generate movement sensor data indicating one or more of: a position of the patient's tooth and an orientation of the patient's tooth; an electromagnetic field generator coupled to one of the one or more aligner bodies; and a processor configured to receive and store the movement sensor data.

In any of these apparatuses, the processor may be configured to repeatedly receive and store the movement sensor data at an interval of between 1 hour and 2 weeks (e.g., every hour, every two hours, every 3 hours, every four hours, every 5 hours, every 6 hours, every 7 hours, every 8 hours, every 9 hours, every 10 hours, every 11 hours, every 12 hours, every 24 hours, every 36 hours, every 48 hours, every 3 days, every 4 days, every 5 days, every week, etc.). The apparatus may therefore include a memory, a clock, a power source, etc.

As mentioned, any of these apparatuses may also include a plurality of force sensors coupled to the aligner body or on attachments configured to couple the aligner body to the patient's teeth. These force sensors may be configured to generate force sensor data indicating one or more of: an amount of force applied to the patient's teeth and a direction of force applied to the patient's teeth. The processor may be configured to receive and store the movement sensor data and the force sensor data.

As mentioned, each movement sensor of the plurality of movement sensors may comprise an electromagnetic target that is configured to generate the movement sensor data. For example, each movement sensor of the plurality of movement sensors comprises a magnet, a flat coil or a cylindrical coil. Any of these apparatuses may also include an electromagnetic field generator, which may be coupled to the aligner body or separate from the aligner body (e.g., on a second aligner worn concurrently with the first aligner, or external to the aligner(s). The movement sensor may be configured to measure the position of the one or more teeth by measuring changes to an applied electromagnetic field.

In general, the processor may be configured to track movement of the patient's teeth relative to each other (e.g., relative to other teeth, the upper jaw, the lower jaw, etc.) based on the movement sensor data.

In general, the movement sensors (e.g., electromagnetic targets) may be positioned on the aligner body or they may be directly mounted to the patient's teeth. For example, the position/movement of the aligner as it is displaced by the patient's teeth may be detected using these movement sensors. Alternatively or additionally, position (e.g. position and orientation) may track directly the movement of the teeth to which the movement sensors (e.g., the electromagnetic target portion of the sensor) is attached. Thus, in any of the method and apparatus variations described herein, it may be beneficial to include the sensors or a portion of the sensor on an attachment. For example, at least some of the movement sensors in the plurality of movement sensors may be on attachments configured to couple the aligner body to the patient's teeth. An attachment is typically bonded to the tooth, and may be used to hold an aligner body in place and/or apply force to the tooth from the aligner. Attachments may be used with multiple aligners in a treatment plan. When a sensor, including but not limited to a movement sensor (including electromagnetic targets) is coupled to or part of an attachment, the attachment may include an electrical contact for communicating with the aligner via an electrical connection, for transmitting data from the sensor.

Any of these apparatuses may also include a power source, a wireless communication circuit coupled to the processor and configured to wirelessly transmit the movement sensor data, a memory, a timer, etc., which may be part of or coupled to the processor.

Also described herein are methods of designing a patient's orthodontic treatment plan, using any of the apparatuses described herein, including (but not limited to) the apparatuses for detecting movement of the teeth. A method may include: receiving movement sensor data from a plurality of movement sensors of an orthodontic appliance having an aligner body with a plurality of teeth receiving cavities shaped to reposition the patient's teeth from an initial arrangement towards a target arrangement according to a first orthodontic treatment plan, wherein the plurality of movement sensors are coupled to the aligner body or on attachments configured to couple the aligner body to the patient's teeth, wherein the movement sensor data indicates one or more of: a position of the patient's tooth and an orientation of the patient's tooth; determining tooth movement from the movement sensor data; and modifying the first orthodontic treatment plan based on the determined tooth movement.

For example, a method of designing a patient's orthodontic treatment plan may include: providing an orthodontic appliance comprising an aligner body with a plurality of teeth receiving cavities shaped to reposition the patient's teeth from an initial arrangement towards a target arrangement according to a first orthodontic treatment plan, wherein a plurality of movement sensors are coupled to the aligner body or on attachments configured to couple the aligner body to the patient's teeth; periodically applying an electromagnetic field from an electromagnetic field generator coupled to the aligner body; receiving, in a processor, movement sensor data from the plurality of movement sensors, wherein the movement sensor data indicates one or more of: a position of the patient's tooth and an orientation of the patient's tooth; determining tooth movement from the movement sensor data; and modifying the first orthodontic treatment plan based on the determined tooth movement by modifying one or more of: a configuration of a plurality of teeth receiving cavities of an aligner body of a second orthodontic appliance to be worn by the patient or the shortening or lengthening the duration of time that the orthodontic appliance is worn by the patient.

Thus, modifying the treatment plan may include adjusting the aligner design and/or adjusting the duration an aligner is worn. For example, modifying may comprise modifying the configuration of a tooth receiving cavity of an aligner body of a second orthodontic appliance to be worn by the patient. Modifying may include modifying the duration of time that the orthodontic appliance is worn by the patient.

Any of the method described herein may include providing attachments configured to couple the aligner body to the patient's teeth. The aligner body may comprise attachment sites for coupling to the attachments.

Any of the method described herein may also include periodically sampling the sensors and/or recording the sensor values. For example, receiving may include receiving the movement sensor data at intervals of between every hour and every 2 weeks. For motion/position sensors using electromagnetic targets, periodically sampling may include applying an electromagnetic field from an electromagnetic field generator coupled to the aligner body. The method may include periodically applying the electromagnetic field from an electromagnetic field generator comprises applying the electromagnetic field between every two hours and every two weeks The method may include receiving, in the processor, force sensor data from a plurality of force sensors coupled to the aligner body or on the attachments, wherein the force sensor data indicates one or more of: an amount of force applied to the patient's teeth and a direction of force applied to the patient's teeth.

Any of these methods may include determining forces acting on the patient's teeth from the force sensor data. Modifying may include modifying the first orthodontic treatment plan based on the determined tooth movement and the forces acting on the patient's teeth.

The data may be transferred to the processor either locally (e.g., on the aligner) or remotely. For example, any of these methods may include wirelessly transmitting the movement sensor data from the orthodontic appliance to the processor, wherein the processor comprises a remote processor. Receiving may include receiving the movement sensor data in the processor wherein the processor is coupled to the orthodontic appliance while the orthodontic appliance is worn in the patient's mouth.

Providing may include providing a plurality of attachments configured to couple the aligner body to the patient's teeth, wherein the aligner body comprises attachment site for coupling to the attachments.

Any of these methods may include receiving, in the processor, force sensor data from a plurality of force sensors coupled to the aligner body or on the attachments, wherein the force sensor data indicates one or more of: an amount of force applied to the patient's teeth and a direction of force applied to the patient's teeth. In addition, the methods may include determining forces acting on the patient's teeth from the force sensor data. Modifying may mean modifying the first orthodontic treatment plan based on the determined tooth movement and the forces acting on the patient's teeth.

Also described herein are orthodontic apparatus for repositioning a patient's teeth and tracking tooth movement in which the sensors are on either or both the attachment and/or the engagement site on the aligner body to which the attachment couples. For example, an apparatus may include: an aligner body comprising a plurality of teeth receiving cavities shaped to reposition the patient's teeth from an initial arrangement towards a target arrangement, the aligner body having a plurality of engagement sites; a plurality of attachments configured to engage the engagement sites and couple the aligner body to the patient's teeth; wherein each of the plurality of attachments comprises a sensor configured to generate sensor data related to the force applied to the patient's teeth or movement of the patient's teeth by the orthodontic appliance; and a processor coupled to the aligner body and configured to receive and store the sensor data.

An orthodontic apparatus for repositioning a patient's teeth and tracking tooth movement may include: an aligner body comprising a plurality of teeth receiving cavities shaped to reposition the patient's teeth from an initial arrangement towards a target arrangement, the aligner body having a plurality of engagement sites on one or more of a buccal or lingual side of the aligner body; a plurality of attachments configured to engage the engagement sites and couple the aligner body to the patient's teeth; a plurality of sensors, wherein each sensor extends at least partially within each of the plurality of engagement sites, wherein each sensor of the plurality of sensors is configured to generate sensor data related to the force applied to the patient's teeth or movement of the patient's teeth by the orthodontic appliance; and a processor coupled to the aligner body and configured to receive and store the sensor data.

The sensor of each of the plurality of attachments may be any type of sensor described herein, including movement (position) sensors, a force or pressure sensor configured to measure force or pressure applied to one or more teeth by the orthodontic appliance, or the like. Each of the plurality of attachments may comprise a force- or pressure-sensitive film, a resistive film, a capacitive film, or a piezoelectric tactile sensor. Each of the plurality of attachments may comprise an electromagnetic target that is configured to generate movement sensor data indicating one or more of: a position of the patient's tooth and an orientation of the patient's tooth; further wherein the aligner body comprises an electromagnetic field generator.

Any of these apparatuses may include an electrical contact between the attachment and the aligner body. The plurality of engagement sites may include openings or concavities formed through the aligner body.

The plurality of engagement site may be located on one or more of a lingual side of the aligner body or a buccal side of the aligner body.

In any of these methods, the processor may be configured to evaluate a performance of the orthodontic appliance, for example, by using the sensor data to determine one or more of: an amount of force or pressure applied to the patient's teeth, a distribution of force or pressure on the patient's teeth, an amount of movement of the patient's teeth, or a movement rate of the patient's teeth. The processor may be configured to evaluate a performance of the orthodontic appliance by determining whether an amount of force or pressure applied to the patient's teeth by the orthodontic appliance is within a targeted range.

The sensor of each of the plurality of attachments may comprise a movement sensor configured to measure movement of one or more of teeth. For example, the movement sensor may be configured to measure the movement of the one or more teeth by measuring changes to an applied electromagnetic field. As mentioned above, any of these apparatuses may include a power source, memory and/or wireless communication circuit coupled to the processor.

Method of using these apparatuses are also described. For example, a method of designing a patient's orthodontic treatment plan may include: receiving sensor data from a plurality of sensors of an orthodontic appliance having an aligner body with a plurality of teeth receiving cavities shaped to reposition the patient's teeth from an initial arrangement towards a target arrangement according to a first orthodontic treatment plan, wherein a plurality of attachments on the patient's teeth engage engagement sites on the aligner body to couple the aligner body to the patient's teeth, wherein the plurality of sensors are on the attachments, determining, in a processor, one or more of: tooth movement and forces on the patient's teeth from the sensor data; and modifying the first orthodontic treatment plan based on the determined one or more of: tooth movement and forces on the patient's teeth from the sensor data.

A method of designing a patient's orthodontic treatment plan may include: receiving sensor data from a plurality of sensors of an orthodontic appliance having an aligner body with a plurality of teeth receiving cavities shaped to reposition the patient's teeth from an initial arrangement towards a target arrangement according to a first orthodontic treatment plan, wherein a plurality of attachments on the patient's teeth each engage an engagement site on the aligner body to couple the aligner body to the patient's teeth, wherein the plurality of sensors are at least partially within the engagement sites, determining, in a processor, one or more of: tooth movement and forces on the patient's teeth from the sensor data; and modifying the first orthodontic treatment plan based on the determined one or more of: tooth movement and forces on the patient's teeth from the sensor data.

As mentioned above, modifying may include modifying the configuration of a tooth receiving cavity of an aligner body of a second orthodontic appliance to be worn by the patient. Modifying may include modifying the duration of time that the orthodontic appliance is worn by the patient. Modifying may comprise modifying the first orthodontic treatment plan based on the determined one or more of: tooth movement and forces on the patient's teeth from the sensor data. In any of the methods described herein, modifying the treatment plan may include modifying any of the components of the treatment plan, including in particular, modifying the appliance delivering the treatment/therapy. For example modifying the treatment plan may comprise modifying one or more characteristic of one or more of the aligners in a sequence of aligners, including, for example, modifying one or more of the shape and/or thickness of the aligner.

Receiving sensor data may comprise receiving sensor data from a force- or pressure-sensitive film, a resistive film, a capacitive film, or a piezoelectric tactile sensor. Receiving sensor data may include receiving force or pressure data applied to the patient's teeth by the orthodontic appliance. Receiving may include receiving the movement sensor data in the processor wherein the processor is coupled to the orthodontic appliance while the orthodontic appliance is worn in the patient's mouth.

Any of the apparatuses described herein may be modular appliances. Thus, the sensing components (e.g., sensor(s), power supply, processor, memory, and/or wireless transmission circuitry, etc.) may be distributed between the orthodontic appliance (e.g., an aligner) an attachment that is directly bonded onto the subject's tooth to which the appliance may attach. An electrical connection (along with the mechanical connection) between the attachment and the appliance (e.g., an engagement site on the appliance) may be used to transmit power and/or sensor data. Thus, when a series of aligners are worn, the patient may swap out portions of the sensing sub-system of the apparatus, including the power supply, memory, processor, etc.

For example, an orthodontic apparatus for repositioning a patient's teeth and for sensing one or more characteristic from the patient's oral cavity may include an aligner body comprising a plurality of teeth receiving cavities shaped to reposition the patient's teeth from an initial arrangement towards a target arrangement, the aligner body having an engagement site; an attachment configured to be bonded to the patient's teeth and to engage with the engagement site on the aligner body and may receive force and/or secure the aligner body to the patient's teeth; a sensor configured to generate sensor data; a processor configured to receive the sensor data from the sensor and do one or more of: store, analyze and transmit the received sensor data; and a first electrical contact on the attachment and a second electrical contact on the aligner body, wherein the first electrical contact and the second electrical contact form an electrical connection when the attachment is engaged with the engagement site; wherein the sensor is on either the attachment or the aligner and wherein the sensor is in electrical communication with the processor through the electrical connection formed by the first electrical contact and the second electrical contact when the attachment is engaged with the engagement site.

The sensor may be on the attachment and the processor is on the aligner body; alternatively, the processor is on the attachment and the sensor is on the aligner body. In some variations the power source on the aligner (e.g., with the sensor on the attachment and/or the memory or other processor components on the attachment or aligner body). Alternatively, the power source may be on the attachment. The processor may comprise one or more of: a memory, a wireless communications circuit, and a timer. As mentioned, these components may be distributed between the aligner body and/or the attachment.

Any sensor may be used (e.g., temperature sensor, pH sensor, force sensor, pressure sensor, etc.). For example, the sensor may comprise a force or pressure sensor configured to measure force or pressure applied to one or more teeth by the orthodontic appliance. The sensor may comprise, for example, a force- or pressure-sensitive film, a resistive film, a capacitive film, or a piezoelectric tactile sensor. The sensor may comprise an electromagnetic target that is configured to generate movement sensor data indicating one or more of: a position of the patient's tooth and an orientation of the patient's tooth; further wherein the aligner body comprises an electromagnetic field generator.

In general, the engagement site may comprise an opening or concavity formed through the aligner body. The engagement site may be located on one or more of a lingual side of the aligner body or a buccal side of the aligner body.

Any of these apparatuses may include a plurality of additional engagement sites on the aligner body and plurality of additional attachments configured to be bonded to the patient's teeth and to engage with the additional engagement sites and may receive force and/or secure the aligner body to the patient's teeth. The sensor(s), processors, memory, power sources, and wireless communications circuitry may be distributed between all of the attachments and the appliance body (e.g., aligner body).

For example, an orthodontic apparatus for repositioning a patient's teeth and for sensing one or more characteristic from the patient's oral cavity may include: an aligner body comprising a plurality of teeth receiving cavities shaped to reposition the patient's teeth from an initial arrangement towards a target arrangement, the aligner body having an engagement site; an attachment configured to be bonded to the patient's teeth and to engage with the engagement site on the aligner body; a sensor on the attachment configured to generate sensor data; a processor on the aligner configured to receive the sensor data from the sensor and do one or more of: store, analyze and transmit the received sensor data; and a first electrical contact on the attachment and a second electrical contact on the aligner body, wherein the first electrical contact and the second electrical contact form an electrical connection when the attachment is engaged with the engagement site; wherein the sensor is in electrical communication with the processor through the electrical connection formed by the first electrical contact and the second electrical contact when the attachment is engaged with the engagement site.

Also described herein are methods of operating any of these modular/distributed aligners, including forming a mechanical and electrical connection between an aligner body and an attachment so that a sensor is electrically coupled to a processor and/or memory and/or power source through the electrical connection.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7C illustrates a system including an orthodontic appliance and an attachment mounted on a tooth.

FIG. 7D is an example of an intraoral device configured to measure mechanical impedance of a tooth or teeth.

DETAILED DESCRIPTION

Figure 1A:
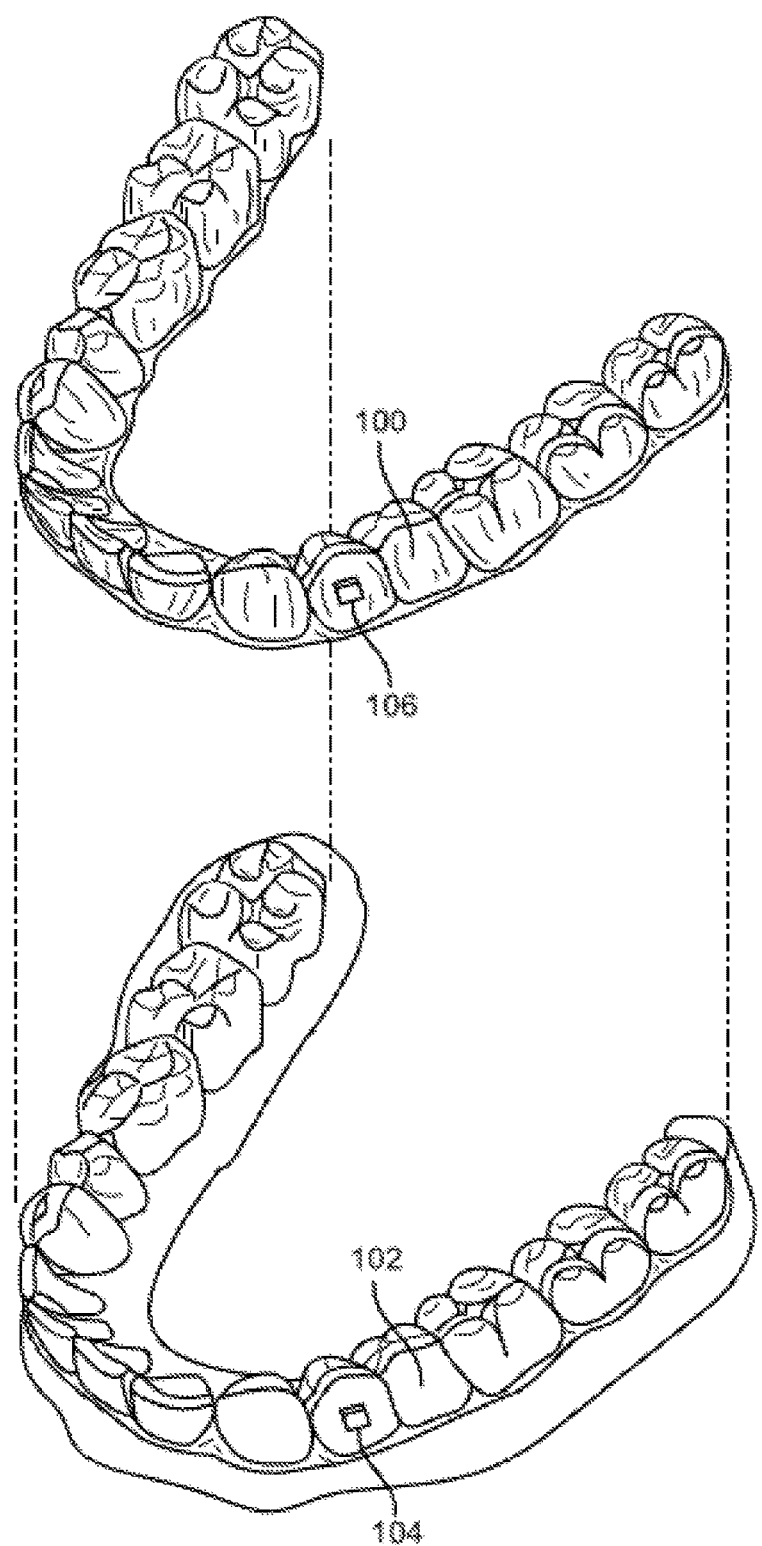
FIG. 1A illustrates a tooth repositioning appliance.

In general, described herein are apparatuses (e.g., systems and devices) and methods for monitoring the progress of appliance-based orthodontic treatment are provided. The apparatuses and methods described herein are exemplified in the context of one or a series of orthodontic aligners, however it should be understood that the principles described herein, and specifically the apparatus and methods described herein, may be applied to any orthodontic appliance, including, but not limited to: orthodontic aligners, palatal expanders, retainers, mouth guards, etc.

The apparatuses described herein are configured to monitor treatment. Thus, any of these apparatuses may be considered monitoring devices. In some embodiments, a monitoring device includes one or more sensors configured to generate sensor data related to repositioning of a patient's teeth using an orthodontic appliance. The sensor data can be processed and analyzed to determine whether the appliance is successfully repositioning the teeth according to the prescribed treatment plan. Advantageously, the embodiments described herein provide an integrated electronic sensing and logging system capable of generating more reliable and accurate aligner performance data, which may be used by the treating practitioner to track treatment progress and adjust the patient's treatment plan if desired. The monitoring devices of the present disclosure can provide high value sensing data useful for adaptive closed-loop treatment planning and appliance design.

In one aspect, a device for monitoring performance of an orthodontic appliance for repositioning a patient's teeth is provided. The device can comprise an orthodontic appliance comprising a plurality of teeth receiving cavities shaped to reposition the patient's teeth from an initial arrangement towards a target arrangement. The device can comprise one or more sensors configured to generate sensor data related to the repositioning of the patient's teeth by the orthodontic appliance. The device can comprise a processor configured to process the sensor data in order to evaluate the performance of the orthodontic appliance in effecting the repositioning of the patient's teeth.

The performance of the orthodontic appliance can be measured in a variety of ways. For example, in some embodiments, the processor is configured to evaluate the performance of the orthodontic appliance by using the sensor data to determine one or more of: an amount of force or pressure applied to the patient's teeth, a distribution of force or pressure on the patient's teeth, an amount of movement of the patient's teeth, or a movement rate of the patient's teeth.

In some embodiments, the one or more sensors comprise a force or pressure sensor configured to measure force or pressure applied to one or more teeth by the orthodontic appliance. The force or pressure sensor can comprise a force- or pressure-sensitive film, a resistive film, a capacitive film, or a piezoelectric tactile sensor. The processor can be configured to evaluate the performance of the orthodontic appliance by determining whether an amount of force or pressure applied to the patient's teeth by the orthodontic appliance is within a targeted range, for example.

In some embodiments, the one or more sensors comprise a movement sensor configured to measure movement of one or more of teeth. The movement sensor can comprise an electromagnetic field generator configured to generate an electromagnetic field. The movement sensor can be configured to measure the movement of the one or more teeth by measuring changes to the electromagnetic field. For instance, the movement sensor can comprise one or more electromagnetic targets arranged to move in response to the movement of the one or more teeth, such that movement of the one or more electromagnetic targets produces changes to the electromagnetic field.

In some embodiments, the one or more sensors comprise a plurality of different sensors operably coupled to different portions of the orthodontic appliance. The one or more sensors can be integrated with the orthodontic appliance, coupled to a tooth, or a combination thereof.

In some embodiments, the processor is integrated with the orthodontic appliance or coupled to a tooth. Alternatively, the processor can be located external to the patient's intraoral cavity. In some embodiments, the device further comprises a communication module configured to transmit one or more of the sensor data or the processed sensor data to a remote device.

In another aspect, a method for monitoring performance of an orthodontic appliance for repositioning a patient's teeth is provided. The method can comprise receiving sensor data related to the repositioning of the patient's teeth by the orthodontic appliance from one or more sensors. The orthodontic appliance can comprise a plurality of teeth receiving cavities shaped to reposition the patient's teeth from an initial arrangement towards a target arrangement. The sensor data can be processed in order to evaluate the performance of the orthodontic appliance in effecting the repositioning of the patient's teeth.

In some embodiments, the performance of the orthodontic appliance is evaluated by using the sensor data to determine one or more of: an amount of force or pressure applied to the patient's teeth, a distribution of force or pressure on the patient's teeth, an amount of movement of the patient's teeth, or a movement rate of the patient's teeth.

In some embodiments, the one or more sensors comprise a force or pressure sensor configured to measure force or pressure applied to the patient's teeth by the orthodontic appliance. The force or pressure sensor can comprise a force- or pressure-sensitive film, a resistive film, a capacitive film, or a piezoelectric tactile sensor, for example. The performance of the orthodontic appliance can be evaluated by determining whether an amount of force or pressure applied to the patient's teeth by the orthodontic appliance is within a targeted range.

In some embodiments, the one or more sensors comprise a movement sensor configured to detect movement of the patient's teeth. The movement sensor can comprise an electromagnetic field generator configured to generate an electromagnetic field. The movement sensor can be configured to measure the movement of the one or more teeth by measuring changes to the electromagnetic field. Optionally, the movement sensor comprises one or more electromagnetic targets arranged to move in response to the movement of the one or more teeth, such that movement of the one or more electromagnetic targets produces changes to the electromagnetic field.

In some embodiments, the one or more sensors comprise a plurality of different sensors operably coupled to different portions of the orthodontic appliance. For example, the one or more sensors can be integrated with the orthodontic appliance, coupled to a tooth, or a combination thereof.

In some embodiments, the processing step is performed by a processor integrated with the orthodontic appliance or a coupled to a tooth. Alternatively, the processor can be located external to the patient's intraoral cavity.

In some embodiments, the method further comprises transmitting one or more of the sensor data or the processed sensor data to a remote device.

The various embodiments of the present disclosure can be used in combination with various types of orthodontic appliances. For example, appliances having teeth receiving cavities that receive and reposition teeth, e.g., via application of force due to appliance resiliency, are generally illustrated with regard to FIG. 1A. FIG. 1A illustrates an exemplary tooth repositioning appliance or aligner 100 that can be worn by a patient in order to achieve an incremental repositioning of individual teeth 102 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g. 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or fewer than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309, 215 and 6,830,450.

Figure 1B:
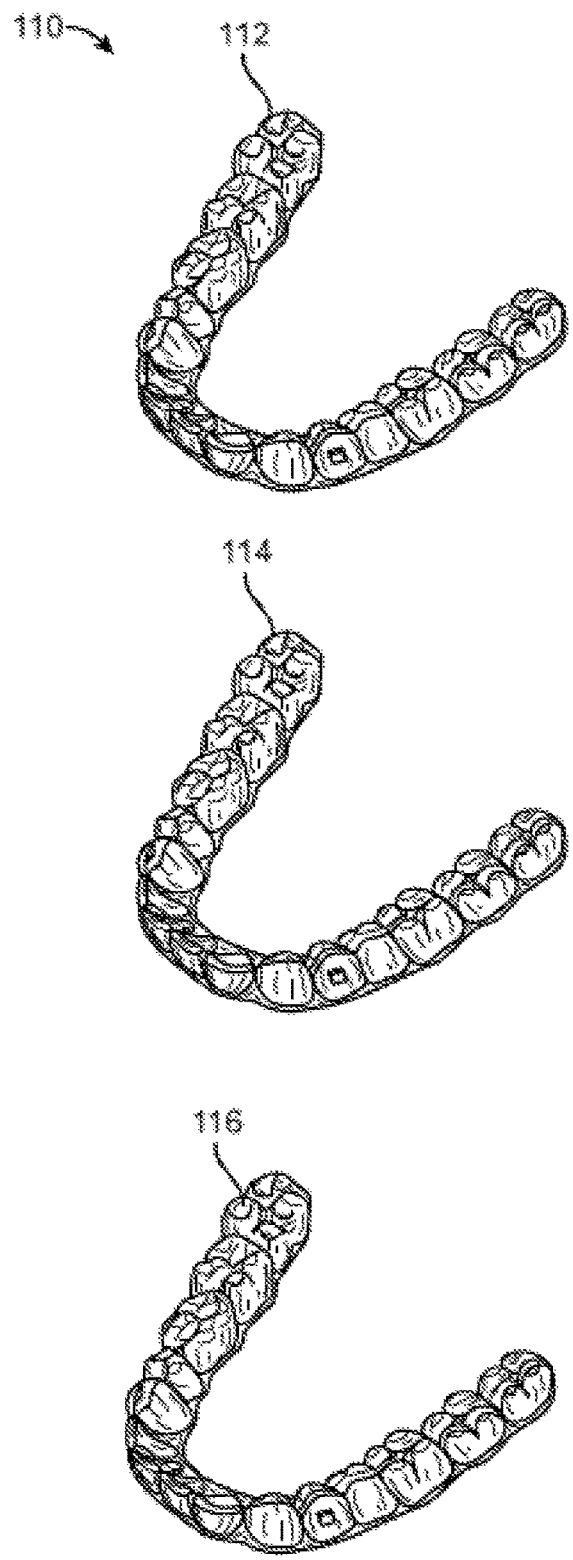
FIG. 1B illustrates a tooth repositioning system.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 1A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

Figure 2:
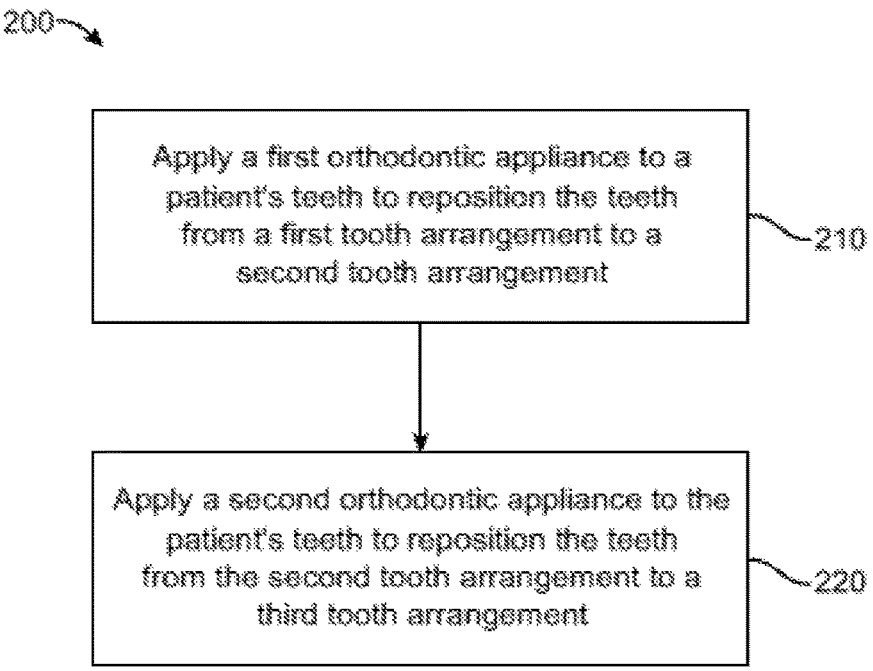
FIG. 2 illustrates a method of orthodontic treatment using a plurality of appliances.

FIG. 2 illustrates a method 200 of orthodontic treatment using a plurality of appliances. The method 200 can be practiced using any of the appliances or appliance sets described herein. In step 210, a first orthodontic appliance is applied to a patient's teeth in order to reposition the teeth from a first tooth arrangement to a second tooth arrangement. In step 220, a second orthodontic appliance is applied to the patient's teeth in order to reposition the teeth from the second tooth arrangement to a third tooth arrangement. The method 200 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (i.e. patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

An orthodontic appliance can be operably coupled to a monitoring device configured to provide data related to tooth repositioning, such as tooth movement data (e.g., magnitude and/or direction of tooth movements, tooth movement rate, etc.) and/or the interaction between the appliance and the patient's teeth (e.g., contact between the appliance and the teeth, the amount of force and/or pressure applied by the appliance to the teeth, distribution of force and/or pressure on the teeth, etc.). Such data can be used to evaluate the performance of the orthodontic appliance for repositioning the patient's teeth, as discussed in greater detail herein. For instance, appliance performance information as described herein can include information regarding whether the force(s), pressure(s), and/or tooth movement(s) produced by an orthodontic appliance correlate with the expected values for the planned orthodontic treatment.

The monitoring devices described herein can be designed for use in the patient's intraoral cavity. For example, the dimensions of a monitoring device may be limited in order to avoid patient discomfort and/or facilitate integration into an orthodontic appliance as discussed below. In some embodiments, a monitoring device has a height or thickness less than or equal to about 1.5 mm, or less than or equal to about 2 mm. In some embodiments, a monitoring device has a length or width less than or equal to about 4 mm, or less than or equal to about 5 mm. The shape of the monitoring device can be varied as desired, e.g., circular, ellipsoidal, triangular, square, rectangular, etc. For instance, in some embodiments, a monitoring device can have a circular shape with a diameter less than or equal to about 5 mm.

A relatively thin and flexible monitoring device can be used to provide a larger surface area while reducing patient discomfort. In some embodiments, the monitoring devices herein are sized to conform to a surface of a tooth crown (e.g., a buccal, lingual, and/or occlusal surface of a tooth crown). For example, a monitoring device having dimensions of about 10 mm by about 5 mm can be used to cover a buccal surface of a molar crown. As another example, a monitoring device having dimensions of about 10 mm by about 20 mm can be used to cover the buccal, occlusal, and lingual surfaces of a tooth crown. A monitoring device can be in contact with a crown of a single tooth, or with crowns of a plurality of teeth, as desired.

The other properties of the monitoring device (e.g., volume, weight) can be designed in order to reduce patient discomfort. For instance, the weight of a monitoring device can be selected not to exceed a level that would exert undesirable forces on the underlying teeth.

In alternative embodiments, a monitoring device may be used primarily for research and characterization purposes, rather than for patient treatment, and thus may not be subject to size constraints for reducing patient discomfort. For example, in embodiments where the monitoring device is used outside the intraoral cavity (e.g., benchtop testing of aligner performance), the size of the monitoring device can be relatively large compared to devices designed for intraoral use.

Figure 3A:
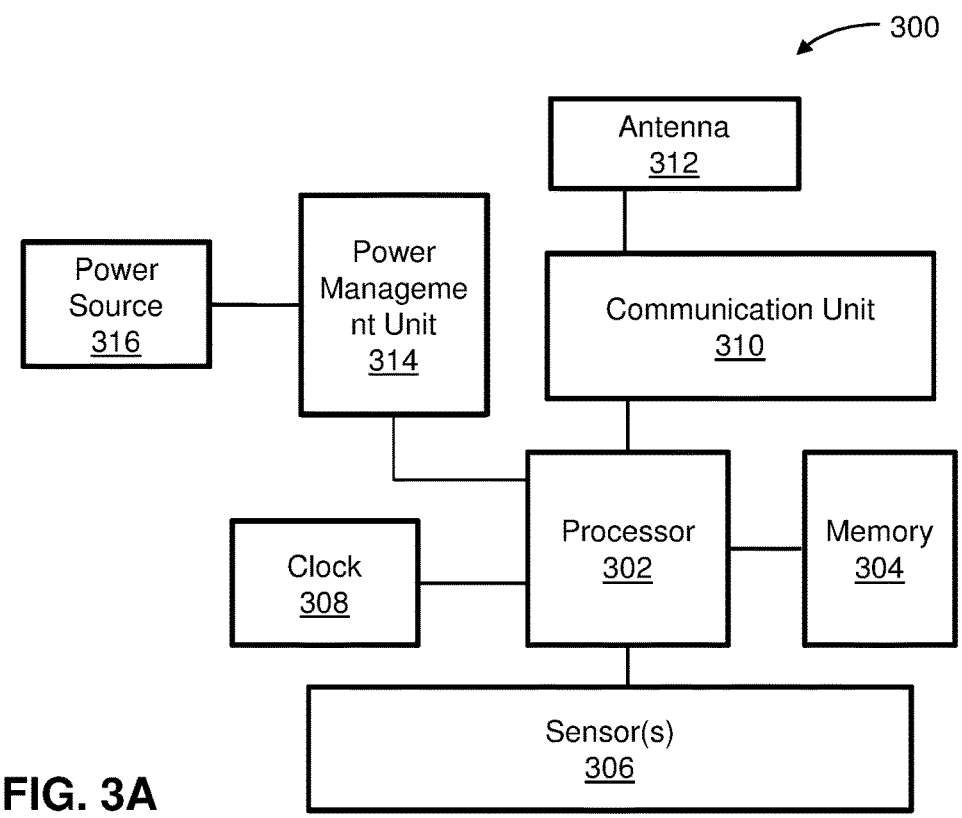
FIG. 3A schematically illustrates a monitoring device.

FIG. 3A schematically illustrates a monitoring device 300, in accordance with embodiments. The monitoring device 300 can be used in combination with any embodiment of the systems and devices described herein, and the components of the monitoring device 300 are equally applicable to any other embodiment of the monitoring devices described herein. The monitoring device 300 can be implemented as an application-specific integrated circuit (ASIC) including one or more of the following components: a processor 302, a memory 304, one or more sensors 306, a clock 308, a communication unit 310, an antenna 312, a power management unit 314, or a power source 316.

The processor 302 (e.g., a central processing unit (CPU), microprocessor, field programmable gate array (FPGA), logic or state machine circuit, etc.), also referred to herein as a controller, can be configured to perform the various methods described herein. The memory 304 encompasses various types of memory known to those of skill in the art, such as RAM (e.g., SRAM, DRAM), ROM (EPROM, PROM, MROM), or hybrid memory (e.g., flash, NVRAM, EEPROM), and the like. The memory 304 can be used to store instructions executable by the processor 302 to perform the methods provided herein. Additionally, the memory can be used to store sensor data obtained by the sensor(s) 306, as discussed in greater detail below.

The monitoring device 300 can include any number of sensors 306, such as one, two, three, four, five, or more (e.g., fourteen, fifteen, sixteen, etc.) sensors. In some embodiments, the use of multiple sensors provides redundancy to increase the accuracy and reliability of the resultant data. Some or all of the sensors 306 can be of the same type. Some or all of the sensors 306 can be of different types. Examples of sensor types suitable for use in the monitoring devices described herein include: touch or tactile sensors (e.g., capacitive, resistive), proximity sensors, movement sensors (e.g., electromagnetic field sensors), force sensors (e.g., force-sensitive resistive or capacitive materials), pressure sensors (e.g., pressure-sensitive resistive or capacitive materials), strain gauges (e.g., resistive- or MEMS-based), electrical sensors, optical sensors (e.g., LED/photodetectors), or combinations thereof.

A sensor 306 can be operably coupled to and/or located at any portion of an orthodontic appliance, such as at or near a distal portion, a mesial portion, a buccal portion, a lingual portion, a gingival portion, an occlusal portion, or a combination thereof. A sensor 306 can be positioned near a tissue of interest when the appliance is worn in the patient's mouth, such as near or adjacent the teeth, gingiva, palate, lips, tongue, cheeks, airway, or a combination thereof. For example, when the appliance is worn, the sensor(s) 306 can cover a single tooth, or a portion of a single tooth. Alternatively, the sensor(s) 306 can cover multiple teeth or portions thereof. In embodiments where multiple sensors 306 are used, some or all of the monitoring devices can be located at different portions of the appliance and/or intraoral cavity. Alternatively, some or all of the sensors 306 can be located at the same portion of the appliance and/or intraoral cavity.

An analog-to-digital converter (ADC) (not shown) can be used to convert analog sensor data into digital format, if desired. The processor 302 can process the sensor data obtained by the sensor(s) 306 in order to determine appliance usage and/or patient compliance, as described herein. The sensor data and/or processing results can be stored in the memory 304. Optionally, the stored data can be associated with a timestamp generated by the clock 308 (e.g., a real-time clock or counter).

In some embodiments, the monitoring device 300 includes a communication unit 310 configured to transmit the data stored in the memory (e.g., sensor data and/or processing results) to a remote device. The communication unit 310 can utilize any suitable communication method, such as wired or wireless communication methods (e.g., RFID, near-field communication, Bluetooth, ZigBee, infrared, etc.). The communication unit 310 can include a transmitter for transmitting data to the remote device and an antenna 312. Optionally, the communication unit 310 includes a receiver for receiving data from the remote device. In some embodiments, the communication channel utilized by the communication unit 310 can also be used to power the device 300, e.g., during data transfer or if the device 300 is used passively.

The remote device can be any computing device or system, such as a mobile device (e.g., smartphone), personal computer, laptop, tablet, wearable device, etc. Optionally, the remote device can be a part of or connected to a cloud computing system ("in the cloud"). The remote device can be associated with the patient, the treating practitioner, medical practitioners, researchers, etc. In some embodiments, the remote device is configured to process and analyze the data from the monitoring device 300, e.g., in order to assess appliance performance, for research purposes, and the like.

The monitoring device 300 can be powered by a power source 316, such as a battery. In some embodiments, the power source 316 is a printed and/or flexible battery, such as a zinc-carbon flexible battery, a zinc-manganese dioxide printed flexible battery, or a solid-state thin film lithium phosphorus oxynitride battery. The use of printed and/or flexible batteries can be advantageous for reducing the overall size of the monitoring device 300 and avoiding patient discomfort. For example, printed batteries can be fabricated in a wide variety of shapes and can be stacked to make three-dimensional structures, e.g., to conform the appliance and/or teeth geometries. Likewise, flexible batteries can be shaped to lie flush with the surfaces of the appliance and/or teeth. Alternatively or in combination, other types of power sources or power storage (e.g., batteries, capacitors, etc.) can be used, such as supercapacitors. In some embodiments, the power source 316 can utilize lower power energy harvesting methods (e.g., thermodynamic, electrodynamic, piezoelectric) in order to generate power for the monitoring device 300. Optionally, the power source 316 can be rechargeable, for example, using via inductive or wireless methods. In some embodiments, the patient can recharge the power source 316 when the appliance is not use. For example, the patient can remove the orthodontic appliance when brushing the teeth and place the appliance on an inductive power hub to recharge the power source 316.

Optionally, the monitoring device 300 can include a power management unit 314 connected to the power source 316. The power management unit 314 can be configured to control when the monitoring device 300 is active (e.g., using power from the power source 316) and when the device 300 is inactive (e.g., not using power from the power source 316). In some embodiments, the monitoring device 300 is only active during certain times so as to lower power consumption and reduce the size of the power source 316, thus allowing for a smaller monitoring device 300.

In some embodiments, the monitoring device 300 includes an activation mechanism (not shown) for controlling when the monitoring device 300 is active (e.g., powered on, monitoring appliance usage) and when the monitoring device 300 is dormant (e.g., powered off, not monitoring appliance usage). The activation mechanism can be provided as a discrete component of the monitoring device 300, or can be implemented by the processor 302, the power management unit 314, or a combination thereof. The activation mechanism can be used to reduce the amount of power used by the monitoring device 300, e.g., by inactivating the device 300 when not in use, which can be beneficial for reducing the size of the power supply 316 and thus the overall device size.

In some embodiments, the monitoring device 300 is dormant before being delivered to the patient (e.g., during storage, shipment, etc.) and is activated only when ready for use. This approach can be beneficial in conserving power expenditure. For example, the components of the monitoring device 300 can be electrically coupled to the power source 316 at assembly, but may be in a dormant state until activated, e.g., by an external device such as a mobile device, personal computer, laptop, tablet, wearable device, power hub etc. The external device can transmit a signal to the monitoring device 300 that causes the activation mechanism to activate the monitoring device 300. As another example, the activation mechanism can include a switch (e.g., mechanical, electronic, optical, magnetic, etc.), such that the power source 316 is not electrically coupled to the other components of the monitoring device 300 until the switch is triggered. For example, in some embodiments, the switch is a reed switch or other magnetic sensor that is held open by a magnet. The magnet can be removably attached to the monitoring device 300, or may be integrated into the packaging for the device 300 or appliance, for example. When the monitoring device is separated from the magnet (e.g., by removing the magnet or removing the device and appliance from the packaging), the switch closes and connects the power source 316. As another example, the monitoring device 300 can include a mechanical switch such as a push button that is manually actuated in order to connect the power source 316. In some embodiments, the activation mechanism includes a latching function that locks the switch upon the first actuation to maintain connectivity with the power source so as to maintain activation of the monitoring device 300. Optionally, the switch for the activation mechanism can be activated by a component in the patient's intraoral cavity (e.g., a magnet coupled to a patient's tooth), such that the monitoring device 300 is active only when the appliance is worn by the patient, and is inactive when the appliance is removed from the patient's mouth. Alternatively or in combination, the switch can be activated by other types of signals, such as an optical signal.

Figure 3B:
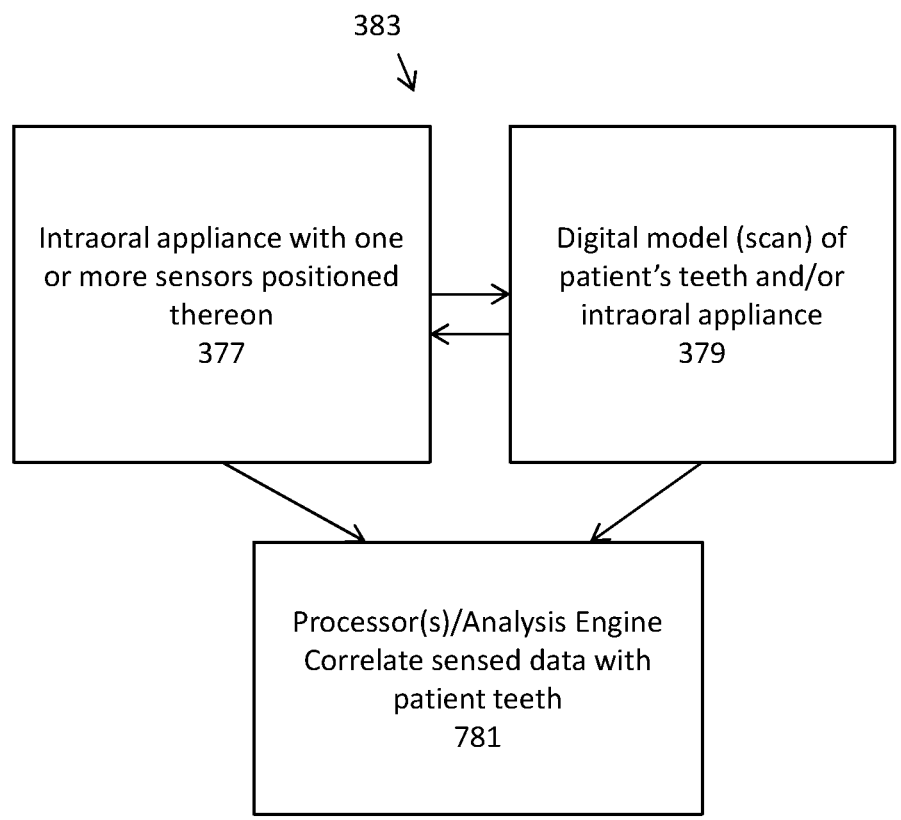
FIG. 3B schematically illustrates a system including any of the intraoral appliances with one or more sensors as described herein, and digital scan data of the appliance and/or patient's teeth. An analysis engine (which may be part of the intraoral appliance or separate from the intraoral appliance) may integrate the digital information and the sensor information, and may relate the specific sensor information to the patient's teeth using the digital scan data.

In general any of the apparatuses described herein may be used in conjunction with digital model(s) or scans or the patient's teeth and/or intraoral appliance. For example, FIG. 3B schematically illustrates a system 383 including an intraoral appliance 377 with one or more sensors, and digital scan data of the appliance and/or patient's teeth 379. An analysis engine 381 (which may be part of the intraoral appliance or separate from the intraoral appliance) may integrate the distal information and the sensor information, and may relate the specific sensor information to the patient's teeth using the digital scan data.

Figure 4:
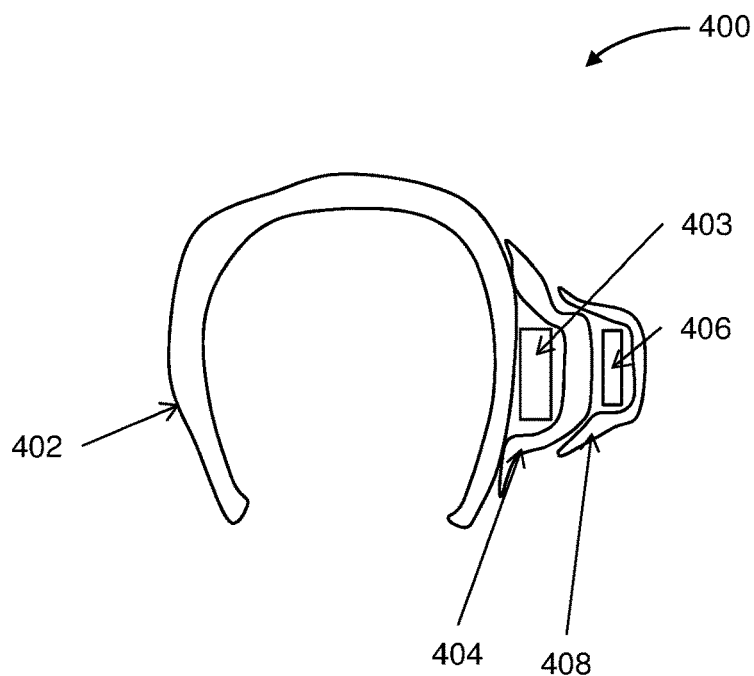
FIG. 4 illustrates a monitoring device with an activation mechanism.

FIG. 4 illustrates a monitoring device 400 with an activation mechanism, in accordance with embodiments. The monitoring device 400, as with all other monitoring devices described herein, can be similar to the monitoring device 300 in FIG. 3A, and can include some or all of the components described herein with respect to such monitoring devices 300. The device 400 is coupled to an orthodontic appliance 402 (e.g., via an encapsulating material 404). The device 400 can include an activation mechanism 403 including a magnetic switch. Prior to use, the device 400 can be removably coupled to a magnet 406 (e.g., using tape 408), and the magnet 406 can hold the magnetic switch in an open position such that the device 400 is inactive. When the appliance 402 is ready for use, the user can remove the magnet 406, thus closing the magnetic switch and connecting the components of the monitoring device 400 to a power source.

The orthodontic appliances and monitoring devices described herein can be configured in many different ways. In some embodiments, an orthodontic appliance as described herein is operably coupled to a single monitoring device. Alternatively, the orthodontic appliance can be operably coupled to a plurality of monitoring devices, such as at least two, three, four, five, or more monitoring devices. Some or all of the monitoring devices may be of the same type (e.g., collect the same type of data). Alternatively, some or all of the monitoring devices may be of different types (e.g., collect different types of data). Any of the embodiments of monitoring devices described herein can be used in combination with other embodiments in a single orthodontic appliance.

A monitoring device can be located at any portion of the appliance, such as at or near a distal portion, a mesial portion, a buccal portion, a lingual portion, a gingival portion, an occlusal portion, or a combination thereof. The monitoring device can be positioned near a tissue of interest when the appliance is worn in the patient's mouth, such as near or adjacent the teeth, gingiva, palate, lips, tongue, cheeks, airway, or a combination thereof. For example, when the appliance is worn, the monitoring device can cover a single tooth, or a portion of a single tooth. Alternatively, the monitoring device can cover multiple teeth or portions thereof. In embodiments where multiple monitoring devices are used, some or all of the monitoring devices can be located at different portions of the appliance. Alternatively, some or all of the monitoring devices can be located at the same portion of the appliance.

A monitoring device can be operably coupled to the orthodontic appliance in a variety of ways. For example, the monitoring device can be physically integrated with the orthodontic appliance by coupling the monitoring device to a portion of the appliance (e.g., using adhesives, fasteners, latching, laminating, molding, etc.). The coupling may be a releasable coupling allowing for removal of the monitoring device from the appliance, or may be a permanent coupling in which the monitoring device is permanently affixed to the appliance. Alternatively or in combination, the monitoring device can be physically integrated with the orthodontic appliance by encapsulating, embedding, printing, or otherwise forming the monitoring device with the appliance. In some embodiments, the appliance includes a shell shaped to receive the patient's teeth, and the monitoring device is physically integrated with the shell. The monitoring device can be located on an inner surface of the shell (e.g., the surface adjacent to the received teeth), an outer surface of the shell (e.g., the surface away from the received teeth), or within a wall of the shell. Optionally, as discussed further herein, the shell can include a receptacle shaped to receive the monitoring device. Exemplary methods for fabricating an appliance with a physically integrated monitoring device (e.g., by incorporating some or all of the components of the monitoring device during direct fabrication of the appliance) are described in further detail herein.

Figure 5A:
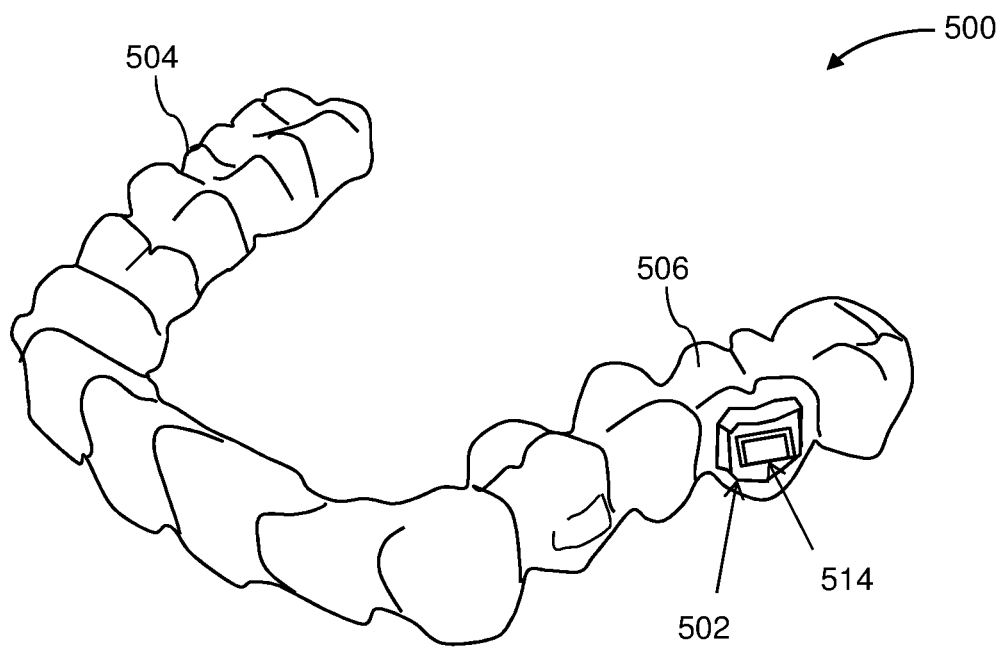
FIG. 5A illustrates an orthodontic appliance including an integrated monitoring device.
Figure 5B:
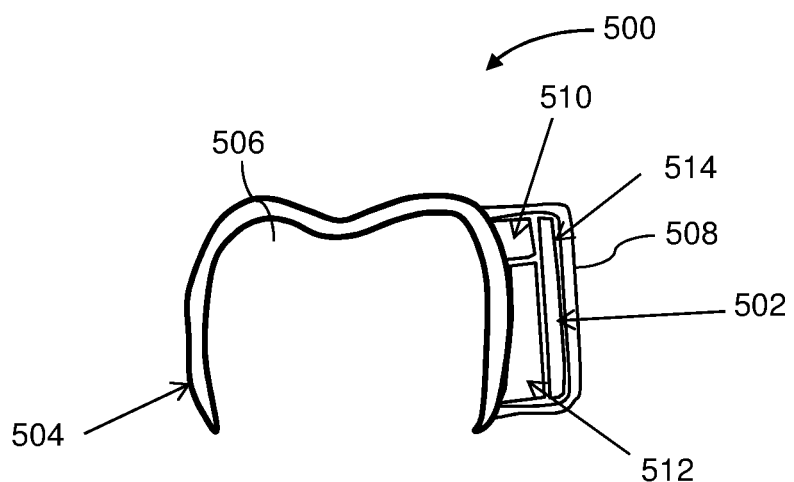
FIG. 5B is a cross-sectional view of the appliance of FIG. 5A.

FIGS. 5A and 5B illustrate an orthodontic appliance 500 including an integrated monitoring device 502, in accordance with embodiments. The appliance 500 includes a shell 504 having a plurality of teeth receiving cavities, and the monitoring device 502 is coupled to an outer, buccal surface of the shell 504 adjacent a tooth receiving cavity 506. In the depicted embodiment, the monitoring device 502 is coupled to a tooth receiving cavity 506 for a molar. It shall be appreciated that in alternative embodiments, the monitoring device 502 can be coupled to other portions of the shell 504, such as an inner surface, a lingual surface, an occlusal surface, one or more tooth receiving cavities for other types of teeth (e.g., incisor, canine, premolar), etc. The monitoring device 502 can be shaped to conform to the geometry of the corresponding appliance portion (e.g., the wall of the cavity 306) so as to provide a lower surface profile and reduce patient discomfort. In some embodiments, the appliance 500 includes a receptacle 508 formed on the outer surface of the shell 504 and the monitoring device 502 is positioned within the receptacle. Exemplary methods for forming an appliance with a receptacle 508 and integrated monitoring device 502 are described in detail below.

The monitoring device 502 can include any of the components previously described herein with respect to the monitoring device 300 of FIG. 3A. For example, the monitoring device 502 can include a sensor 510, a power source 512 (e.g., a battery), and/or a communication unit 514 (e.g., a wireless antenna). The arrangement of the components of the monitoring device 502 can be varied as desired. In some embodiments, the sensor 508 is located adjacent to the tooth receiving cavity 506. A gap can be formed in the shell 504 adjacent to the sensor 510 so as to permit direct access to the received tooth. The communication unit 514 (or a component thereof, such as an antenna) can be located adjacent to or on the outer surface of the receptacle 408 so as to facilitate data transmission.

In some embodiments, some of the components of a monitoring device may be packaged and provided separately from other components of the device. For example, a monitoring device can include one or more components that are physically integrated with a first orthodontic appliance and one or more components that are physically integrated with a second orthodontic appliance. The first and second orthodontic appliances can be worn on opposing jaws, for example. Any of the components of a monitoring device (e.g., components of the device 300 of FIG. 3A) can be located on an appliance for the upper jaw, an appliance for the lower jaw, or a combination thereof. In some embodiments, it is beneficial to distribute the components of the monitoring device across multiple appliances in order to accommodate space limitations, accommodate power limitations, and/or improve sensing, for example. Additionally, some of the components of a monitoring device can serve as a substrate for other components (e.g., a battery serves as a substrate to an antenna).

Figure 6:
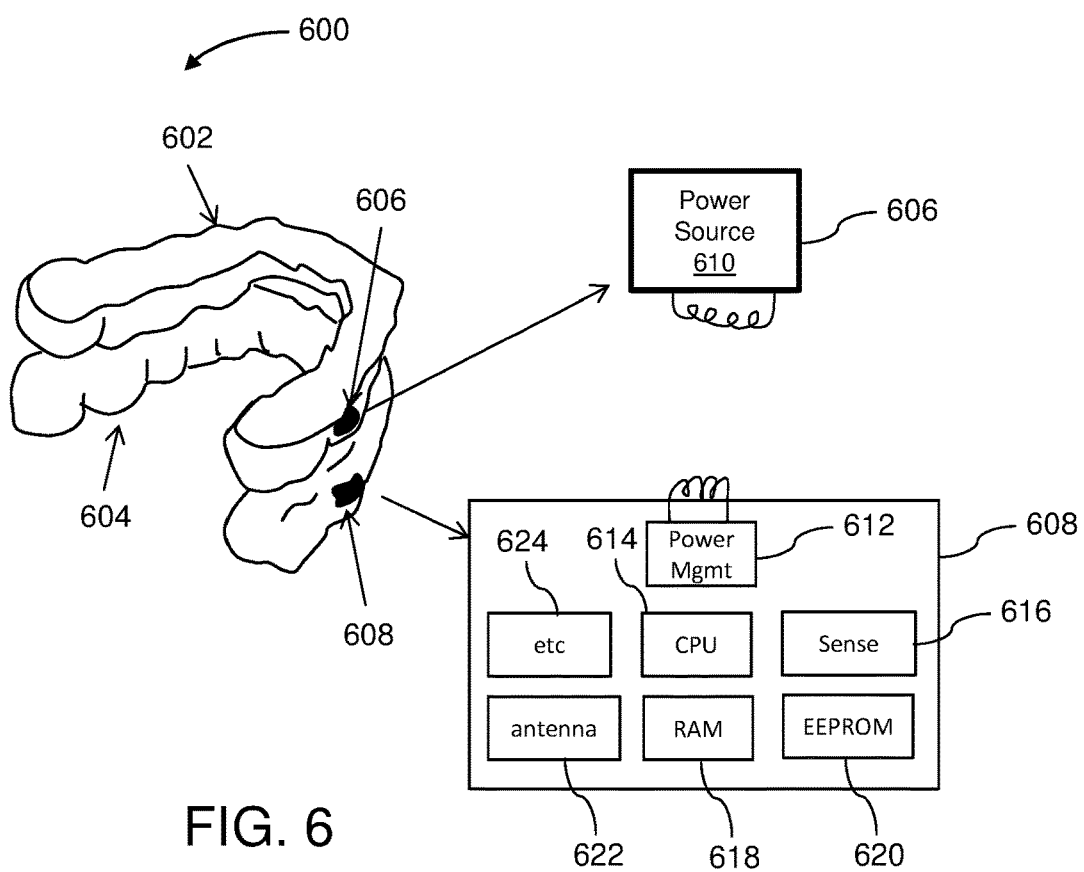
FIG. 6 illustrates a monitoring system including a first appliance and a second appliance.

FIG. 6 illustrates a monitoring system 600 including a first appliance 602 and a second appliance 604, in accordance with embodiments. The first appliance 602 can be shaped to receive teeth of a patient's upper arch and the second appliance 604 can be shaped to receive teeth of a patient's lower arch. The system 600 can include a monitoring device separated in to a first subunit 606 physically integrated with the first appliance 602 and a second subunit 608 physically integrated with the second appliance 604. In some embodiments, the first subunit 606 is a power supply subunit including a power source 610, and the second subunit 608 is a sensing subunit including the remaining components of the monitoring device, such as a power management unit 612, processor (e.g., CPU 614), sensor 616, memory (e.g., RAM 618 such as SRAM or DRAM; ROM such as EPROM, PROM, or MROM; or hybrid memory such as EEPROM 620, flash, or NVRAM), communication unit (e.g., antenna 622), or any other component 624 described herein (e.g., with respect to the monitoring device 300 of FIG. 3A). The first subunit 606 and second subunit 608 can be operably coupled to each other via inductive coupling between the power supply 610 and power management unit 612, e.g., when the first appliance 602 and second appliance 604 are brought into proximity with each other by the closing of the patient's jaws.

It shall be appreciated that the configuration of FIG. 6 can be varied as desired. For example, the first subunit 606 can be physically integrated with the second appliance 604 and the second subunit 608 can be physically integrated with the first appliance 602. As another example, the distribution of the monitoring device components between the first subunit 606 and second subunit 608 can differ from the depicted embodiment.

Alternatively or in combination, a monitoring device can include one or more components that are physically integrated with an orthodontic appliance and one or more components that are physically integrated with another device external to the patient's intraoral cavity. For example, the external device can be a wearable device (e.g., headgear, smart watch, wearable computer, etc.) worn on another portion of the patient's body. As another example, the external device can be a power hub, a mobile device, personal computer, laptop, tablet, etc. Any of the components of a monitoring device (e.g., components of the device 300 of FIG. 3A) can be located on an external device. In some embodiments, the monitoring device includes a communication unit and antenna integrated into the orthodontic appliance that transmits sensor data from the patient's intraoral cavity to the external device, and optionally receives data from the external device. The monitoring device components integrated into the external device can provide additional functionality (e.g., processing and/or analysis capabilities) that augments the functionality of the monitoring device components within the orthodontic appliance. The monitoring device components within the orthodontic appliance may be capable of operating with or without the augmented functionalities.

Alternatively or in combination, a monitoring device can include one or more components that are physically integrated with an orthodontic appliance and one or more components that are located in the patient's intraoral cavity separate from the appliance. The intraoral components can be positioned so as to interact with (e.g., physically contact, communicate with) the integrated components in the appliance when the appliance is worn. In some embodiments, the intraoral components are coupled to a portion of the intraoral cavity, such as a crown of the patient's tooth. For instance, the intraoral components can be physically integrated into an attachment mounted on a patient's tooth. Alternatively or in combination, the monitoring device can be surgically implanted, e.g., in the bone of the patient's jaw. Any of the components of a monitoring device (e.g., components of the device 300 of FIG. 3A) can be located in the patient's intraoral cavity rather than in the orthodontic appliance. In some embodiments, the appliance and integrated components can be removed from the patient's mouth independently of the intraoral components. Advantageously, this approach may reduce costs by allowing the same device components to be used with multiple different appliances, e.g., when applying a sequence of shell appliances to reposition the patient's teeth.

FIGS. 7A-7C illustrates a system 700 including an orthodontic appliance 702 and an attachment 704 mounted on a tooth 706. The appliance 702 can include a shell with a tooth receiving cavity shaped to receive the tooth 706 and a receptacle shaped to accommodate the attachment (attachment 704) on the tooth 706. In some embodiments, the system 700 includes a monitoring device having a first subunit physically integrated into the appliance 702 (e.g., according to any of the methods described herein) and a second subunit physically integrated into the attachment 704. In some embodiments, the second subunit integrated into the attachment 704 includes the relatively bulky components of the monitoring device, such as the power source, memory, and/or sensors. For example, the attachment 704 can include a battery or other power source operably coupled to the monitoring device components integrated into the appliance 702, e.g., via inductive coupling or direct contact using electrodes 708. In alternative embodiments, this configuration can be reversed, with the power source mounted in the appliance 702 and the remaining monitoring device components located in the attachment 704. This approach can reduce costs when multiple appliances are used, since only the power source is replaced with each new appliance. As another example, the attachment 704 can include a passive sensing element driven by one or more monitoring device components located in the appliance 702. In yet another example, the attachment 704 can include a conductive element used to trigger a switch integrated in the appliance 702.

The monitoring devices of the present disclosure may utilize many different types and configurations of sensors. The description below of certain exemplary monitoring devices is not intended to be limiting, and it shall be appreciated that the features of the various embodiments described herein can be used in combination with features of other embodiments. For example, the monitoring devices discussed below may also include any of the components previously described with respect to the monitoring device 300 of FIG. 3A. A single monitoring device can include any combination of the sensor types and sensor configurations described herein.

The monitoring devices herein may include one or more force and/or pressure sensors for evaluating appliance performance. For example, the monitoring device can include a force- and/or pressure-sensitive material, such as a film or sheet. The force and/or pressure sensors described herein can be resistive sensors, capacitive sensors, strain gauges, piezocrystal sensors, or combinations thereof. In some embodiments, a force and/or pressure sensor includes a resistive material positioned between two thin electrodes in an orthodontic appliance, and the resistance of the material may increase or decrease as force and/or pressure is exerted on the material, e.g., by the interaction between the teeth and the appliance.

A monitoring device can include a single force and/or pressure sensor, or a plurality of force and/or pressure sensors. The sensors can be positioned at any location in the appliance, such on an inner surface, an outer surface, a buccal surface, a lingual surface, an occlusal surface, a mesial portion, a distal portion, a gingival portion, or a combination thereof. In embodiments where the orthodontic appliance includes a shell with a plurality of teeth receiving cavities, the sensors can be positioned on the inner surfaces of the teeth receiving cavities. Optionally, at least some sensors can be located on an outer surface of the appliance, such as an occlusal surface, in order to measure the force and/or pressure generated by contact between the upper and lower teeth.

The sensors can be positioned to be near certain teeth when the appliance is worn, e.g., near teeth to be repositioned and/or at locations where the appliance is expected to exert force on the teeth. For example, force and/or pressure sensors can be located at or near the buccal, lingual, and/or occlusal surfaces of a tooth to be repositioned so as to provide a map of force and/or pressure values over the tooth crown. In some embodiments, the monitoring device is configured to obtain data from buccal, lingual, and occlusal sensors in a predetermined order and at a desired frequency in order to provide a force and/or pressure map over the buccal, lingual, and occlusal surfaces. Alternatively or in combination, if the appliance is shaped to engage an attachment mounted on a tooth in order to exert force onto the tooth, a force and/or pressure sensor can be located at or near the location of engagement between the appliance and the attachment.

The force and/or pressure sensors can be configured to generate measurement data indicative of the contact force and/or pressure (e.g., amount, magnitude, direction, distribution, etc.) between the appliance and one or more of the patient's teeth. Optionally, the force and/or pressure sensors can be configured to generate measurement data indicative of the contact force and/or pressure between the appliance and an attachment coupled to the teeth. The measurement data can be processed (e.g., by the monitoring device or a remote device) to determine whether the measured force and/or pressure values are within a targeted range, e.g., for repositioning teeth, creating anchorage, etc. In some embodiments, the measurement data is used to compute the rate of change in the pressure and/or force applied to the teeth, which may correlate to the tooth movement rate. The rate of change of force and/or pressure can also be used to determine the stress relaxation of the appliance over time. Optionally, the measurement data can be used to compute other biomechanical parameters relevant to tooth repositioning, such as one or more moments applied to a tooth, one or more force couples applied to a tooth, and/or a ratio between the forces and moments applied to a tooth by the appliance (force-moment ratio).

Any of the apparatuses (e.g., monitoring devices) described herein may be configured to determine mechanical impedance of the teeth and/or intraoral appliance using the force applied to the teeth and/or appliance. For example, any of the apparatuses described herein may be configured to derive a mechanical impedance of a tooth, multiple or groups of teeth, and/or the appliance. Generally, mechanical impedance may be referred to as the resistance to motion given an applied force:

$$Z(w)=F(w)/v(w), \text{ where } F=\text{force}, v=\text{velocity and } w=\text{angular frequency}.$$

FIG. 7D illustrates one example of a section through an intraoral appliance 977 (showing in this example as an aligner) including a motion sensor 971 (such as an accelerometer) and one or more force sensors 969, 969', 969". Alternatively or additionally, one or more of the motion sensor and force sensor(s) may be positioned directly on the teeth (including on an attachment adapted to receive force from the intraoral appliance and/or secure the intraoral appliance to the teeth) and may communicate with a processor/analysis engine, battery, communications circuitry, etc. on the aligner.

Figure 7E:
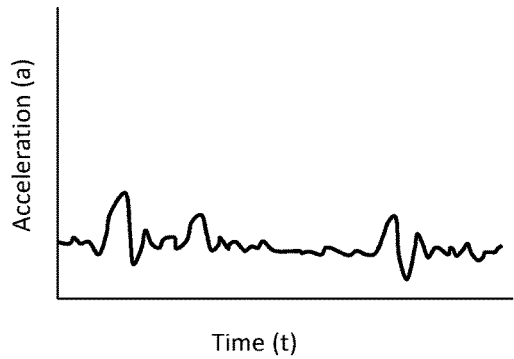
FIG. 7E graphically illustrates the detection of acceleration over time at a particular tooth (or an aligner portion corresponding to a particular tooth).
Figure 7F:
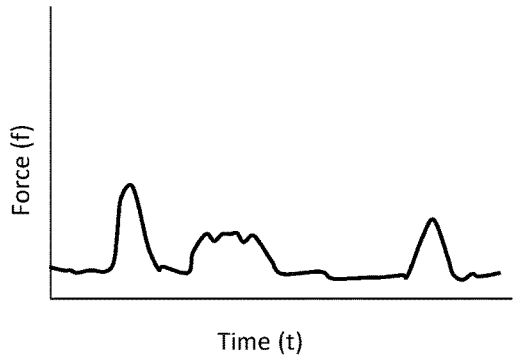
FIG. 7F graphically illustrates the detection of force over time at the same tooth (or aligner region) for which acceleration was determined as shown in FIG. 7E. An intraoral device configured to measure mechanical impedance such as the apparatus shown in FIG. 7D may correlate the acceleration over time and the force over time to estimate mechanical impedance for the tooth.

The processor/analysis engine may then use the motion (e.g., acceleration) data over time, an example of which is shown in FIG. 7E, and corresponding force data over time, an example of which is shown in FIG. 7F, and may correlate this data to estimate mechanical impedance.

Alternatively or additionally, the system may estimate mechanical impedance based on underdamped second order system (e.g., as a logarithmic decrement of an underdamped second order system). In this case, the apparatus may be configured to measure the teeth (and/or appliance) response to a perturbing force, such as an input vibration or force applied to the teeth. For example, the apparatus may be configured to measure the free vibration response to a mechanical impulse input. The apparatus may then determine the peak-to-peak decay of the underdamped oscillation and the period of the system; from these values, the apparatus may then derive the damped natural frequency, the natural frequency, and a damping ratio. In a second order system, these values may define the impedance.

For linear systems, the apparatus may fit parameter of a parametric model of the mechanical impedance to a measured bode plot. For non-linear system, the apparatus may use generalized frequency response functions to analyze non-linear systems (e.g., forced vibrations response, sinusoidal frequency sweeps, etc., including machine learning).

Figure 7G:
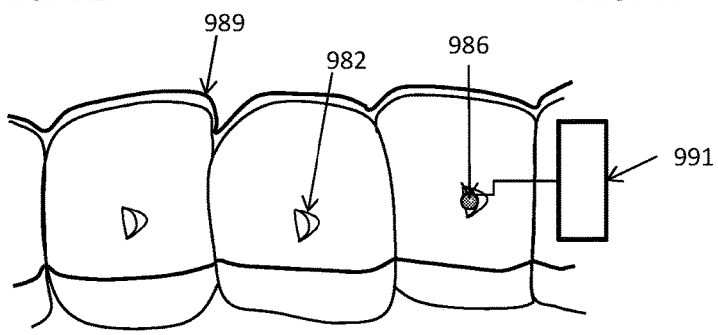
FIG. 7G shows a portion of an intraoral appliance configured to measure mechanical impedance. In this example, one or more motion sensors (e.g., accelerometers) may be coupled to the tooth (as part of the attachment, as shown) and may communicate with electronic components on the intraoral appliance (e.g., memory, processor, power supply, wireless communications, etc.). The apparatus may also include or may be used in conjunction with a mechanical actuator to provide a known (or measured) perturbing vibration, and the processor may use the known force input with the output from the accelerometer to determine mechanical impedance for the tooth/teeth.

For example, FIG. 7G shows a side view of another example of an apparatus for measuring mechanical impedance of a tooth or teeth. In this example, a plurality of attachments 982 are used to secure an orthodontic appliance (e.g., aligner 989) to the teeth. The aligner includes a processor 991, wireless communication circuitry, and may include additional hardware, software and/or firmware for detecting sensor data to determine mechanical impedance of the teeth and/or aligner. The attachments may include one or more sensors, including motion (e.g., accelerometers) and/or force sensors; these one or more sensors may communicate directly (e.g., via electrical contact) with the processor 991 on the aligner.

In FIG. 7G, this configuration may be used as described above, and/or may be used to determine a frequency response to an applied input signal. For example, any of these apparatuses may include an actuator to apply a vibration or force input to the teeth (e.g., a vibration motor, miniature piston, etc.). The force applied by the actuator may be measured or estimated and used in conjunction with the detected response (e.g., motion/acceleration data). Alternatively, the apparatus my take into account naturally occurring force inputs (e.g., masticatory forces), and may measure or estimate them; as mentioned above, using one or more force sensors. The force data as well as the response movement/acceleration data may be used to determine mechanical impedance.

The resulting mechanical impedance data may then be used to assess the health of the tooth movement.

Figure 8A:
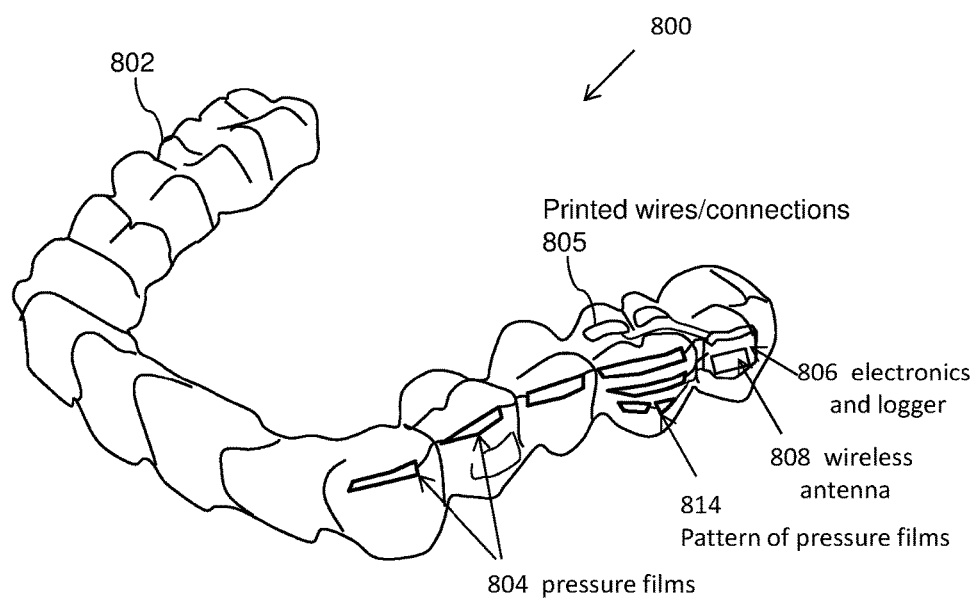
FIG. 8A illustrates a monitoring device configured to measure force and/or pressure between an orthodontic appliance and the patient's teeth.

FIG. 8A illustrates a monitoring device 800 configured to measure force and/or pressure between an orthodontic appliance 802 and the patient's teeth. The device 800 includes a plurality of force and/or pressure sensors 804 (e.g., pressure-dependent resistive films) electrically coupled (e.g., via printed wires 805 or other connecting elements) to a controller 806. The plurality of force and/or pressure sensors 804 can be patterned on the inner surface of the appliance 802 so as to generate sensor data indicative of the force and/or pressure between the appliance 802 and the patient's teeth. In some embodiments, the appliance 802 includes a plurality of teeth receiving cavities and the force and/or pressure sensors 804 are located on the buccal, lingual, and/or occlusal surfaces of the cavities. The controller 806 can include components (e.g., as previously described with respect to FIG. 3A) configured to process the force and/or pressure data in order to evaluate the performance of the appliance 802 in repositioning teeth, as described herein. Optionally, the controller 806 can include a wireless antenna 808 for transmitting the sensor data and/or processing results to a remote device, as described herein.

Figure 8B:
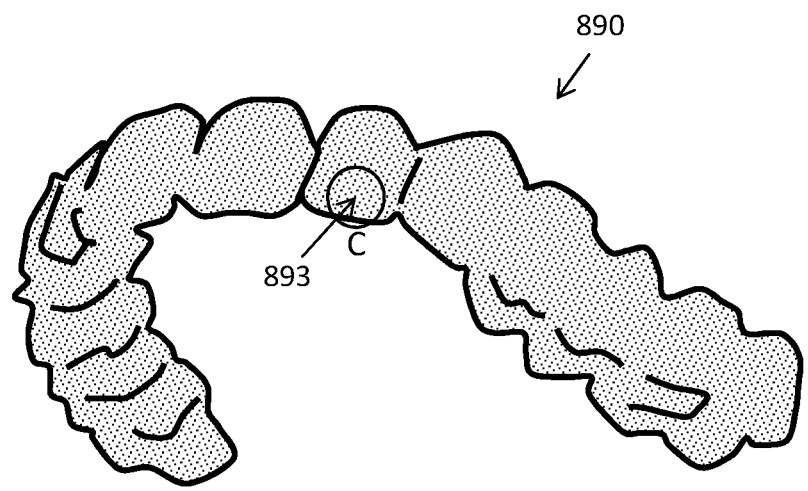
FIG. 8B illustrates an example of an intraoral appliance in which the majority of the aligner surface comprises a capacitive touch-sensor material.
Figure 8C:
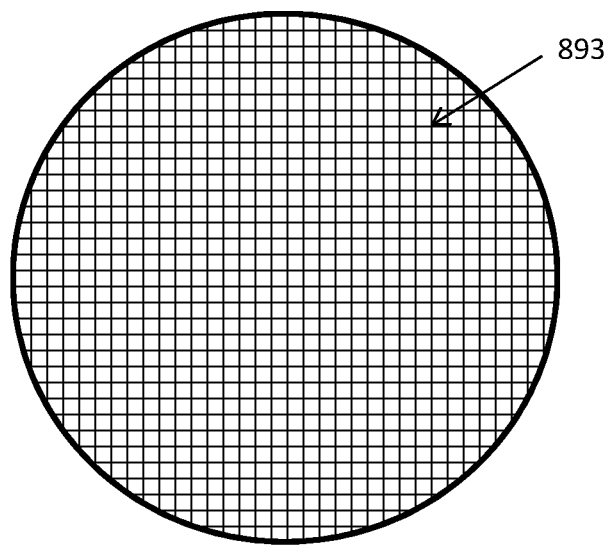
FIG. 8C illustrates an enlarged view, showing the grid pattern of the capacitive touch sensor that is distributed across the surface of the intraoral appliance of FIG. 8B.

In some variations, the majority of (or all of) the intraoral appliance (shown in this example as an aligner, but as mentioned above, may be configured as any other intraoral appliance) may include a capacitive touch-sensor material. In FIG. 8B, the aligner 890 includes a formed surface of capacitive touch-sensor material 893. FIG. 8C shows an enlarged view, showing a grid pattern of the capacitive touch sensor that may be distributed across the surface of the intraoral appliance of FIG. 8B.

The capacitive touch sensor may relate intensity and location of touch information, and may derive force (force moment, and force direction) on the patient's teeth from the intraoral appliance. In some variations the appliance may include one or more processors for receiving touch information from the grid of capacitive sensors and may correlate this information with applied force on the teeth by the apparatus. For example, the capacitive touch data may be correlate to particular teeth using a digital model of the patient's teeth and/or aligner (as discussed above generally in FIG. 3B).

Figure 9A:
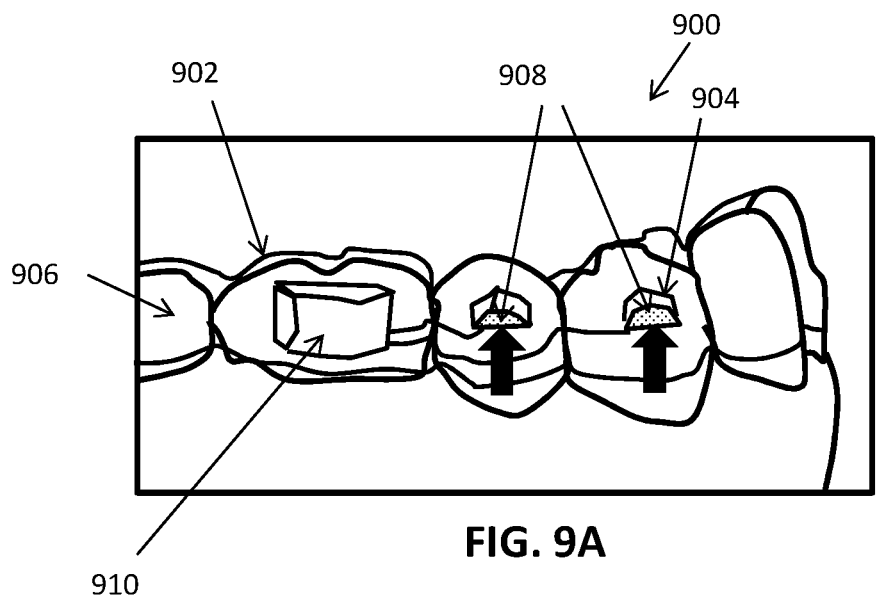
FIG. 9A illustrates a monitoring device configured to measure force and/or pressure between an orthodontic appliance and one or more attachments on a patient's teeth.
Figure 9B:
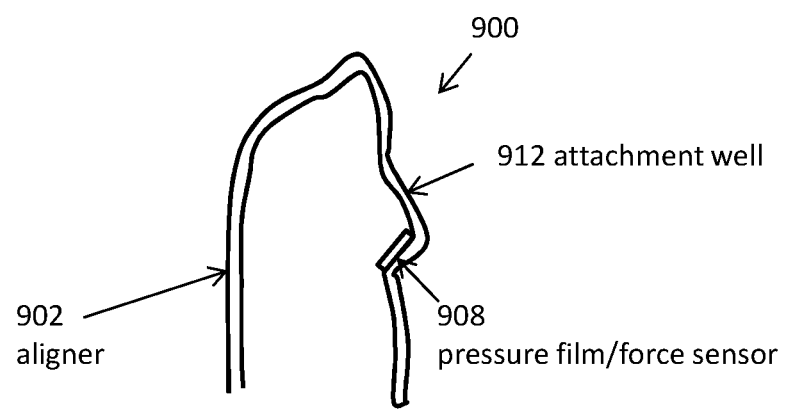
FIG. 9B is a cross-sectional view of the device of FIG. 9A.

FIGS. 9A and 9B illustrate a monitoring device 900 configured to measure force and/or pressure between an orthodontic appliance 902 and one or more attachments 904 on a patient's teeth 906. The device 900 includes a plurality of force and/or pressure sensors 908 (e.g., pressure-dependent resistive films) electrically coupled to a controller 910. The plurality of force and/or pressure sensors 908 can be patterned on the inner surface of the appliance 902 so as to generate sensor data indicative of the force and/or pressure between the appliance 902 and the attachments 904 on the patient's teeth 906. In some embodiments, the appliance 902 includes a plurality of teeth receiving cavities formed with one or more receptacles 912 to receive the corresponding attachments 904 on the patient's teeth, and the pressure and/or force sensors 908 can be positioned the inner surface of one or more receptacles 912. The controller 910 can include components (e.g., as previously described with respect to FIG. 3A) configured to process the sensor data to determine whether the appliance 902 is being worn.

In some embodiments, a monitoring device is configured to assess appliance performance by measuring a response signal to a force and/or pressure impulse signal delivered to the intraoral cavity. For example, the monitoring device can include an actuator (e.g., a miniature piston, vibration motor, or piezoelectric crystal) configured to deliver a force and/or pressure impulse signal to a patient's tooth. A vibration response signal can be recorded with a motion sensor (e.g., an accelerometer) in contact with the tooth. Model-fitting and system identification methods can be used to deduce mechanical properties of the tooth-periodontal ligament (PDL)-alveolar bone system based on the response signal. Statistical and experimental methods can be used to correlate the response signal response with different phases of tooth movement, such as movement due to orthodontic forces applied by an appliance shell, since the stiffness of the tooth-PDL may vary with different stages of tooth movement. The response may also be correlated with and used to evaluate tooth, root, and/or PDL health.

Alternatively or in combination, other types of sensors can be used to indirectly measure the forces and/or pressures applied to the teeth by an appliance. For example, in some embodiments, the application of force and/or pressure to a patient's teeth produces electrical currents (for example, via the piezoelectric effect) in structures of the mouth. Compression of bone and collagen may result in movement of electrons in the crystal lattice, and application of force on the teeth can result in a short piezoelectric effect on the alveolar bone, which may be detected by appropriate receiving sensors such as electrodes. Electrical signals produced by alveolar and periodontal ligaments (PDL) when under load can stimulate changes in bone metabolism. This piezoelectric effect can be measured to determine when a tooth is loaded or overloaded by an appliance. Electrical sensors such as electrodes may also be used to detect these electrical signals, for example, by monitoring changes in voltage.

Alternatively or in combination, the monitoring devices herein can include one or more tactile sensors that respond to direct contact with the patient's teeth. The tactile sensors described herein can be capacitive sensors, resistive sensors, inductive sensors, or piezoelectric sensors, for example. For example, the tactile sensor can be a piezoelectric sensor including one or more materials that exhibit piezoelectric properties, such as quartz, ceramics, or polymers (e.g., polyvinylidene fluoride (PVDF)).

In some embodiments, a tactile sensor can be a sensor array that capable of detecting contact over a two-dimensional surface area. Optionally, a tactile sensor can be provided as a clear, thermoformable screen or film capable of conforming to the shape of the appliance. Some types of tactile sensors may only be capable of providing contact data (e.g., binary data indicating the presence or absence of direct contact), while other types of tactile sensors may also be capable of providing other types of data in addition to contact data (e.g., resistive tactile sensors capable of providing force and/or pressure data).

A monitoring device can include a single tactile sensor, or a plurality of tactile sensors. The sensors can be positioned at any location in the appliance, such on an inner surface, an outer surface, a buccal surface, a lingual surface, an occlusal surface, a mesial portion, a distal portion, a gingival portion, or a combination thereof. In embodiments where the orthodontic appliance includes a shell with a plurality of teeth receiving cavities, the sensors can be positioned on the inner surfaces of the teeth receiving cavities. Optionally, at least some sensors can be located on an outer surface of the appliance, such as an occlusal surface in order to detect contact between the upper and lower teeth.

The sensors can be positioned to be near certain teeth when the appliance is worn, e.g., near teeth to be repositioned and/or at locations where the appliance is expected to exert force on the teeth. For example, tactile sensors can be located at or near the buccal, lingual, and/or occlusal surfaces of a tooth to be repositioned so as to provide a map of contact points over the tooth crown. In some embodiments, the monitoring device is configured to obtain data from buccal, lingual, and occlusal sensors in a predetermined order and at a desired frequency in order to provide a contact map over the buccal, lingual, and occlusal surfaces. Alternatively or in combination, if the appliance is shaped to engage an attachment mounted on a tooth, a tactile sensor can be located at or near the location of engagement between the appliance and the attachment.

The tactile sensors can be configured to generate measurement data indicative of the contact between the appliance and one or more of the patient's teeth. Optionally, the tactile sensors can be configured to generate measurement data indicative of the contact between the appliance and an attachment coupled to the teeth. The measurement data can be processed (e.g., by the monitoring device or a remote device) to determine whether the contacts between the patient's teeth and appliance are consistent with the prescribed treatment plan.

Alternatively or in combination, a monitoring device can include one or more movement sensors for measuring the movements (e.g., translational and/or rotational movements) of one or more teeth. For example, a movement sensor can be used track the movements of one or more teeth relative to the underlying jaw (e.g., mandible or maxilla). As another example, a movement sensor can be used to track the movements of a first set of one or more teeth relative to a second set of one or more teeth, such as when tracking the movements of opposite sides of a single arch during arch or palate expansion. Optionally, a movement sensor can be used to track movements of the upper and lower arches relative to each other, such as when correcting the relative positioning of the arches in order to treat overbite or underbite.

Various types of movement sensors can be used. In some embodiments, a movement sensor includes an electromagnetic field generator (e.g., an electromagnetic coil, generator antenna) integrated into an orthodontic appliance or an attachment mounted on a patient's tooth. The generator can be configured to generate an electromagnetic field (e.g., electric field, magnetic field, or combination thereof) within the intraoral cavity. The movement sensor can also include one or more electromagnetic targets (e.g., a cylindrical or flat coil, magnet, etc.) integrated into an orthodontic appliance (e.g., the same appliance as the generator, a different appliance worn on the opposite jaw, or a combination thereof). The electromagnetic targets can be positioned in the appliance at or near locations where tooth movement is expected to occur (e.g., coupled to teeth receiving cavities of teeth to be repositioned), such that the movements of the teeth produce corresponding movements of the electromagnetic targets. Alternatively or in combination, the monitoring device can include one or more electromagnetic targets integrated into an attachment coupled to the patient's teeth, such that the movements of the teeth and associated targets are directly correlated.

In some embodiments, the electromagnetic targets passively affect the electromagnetic field produced by the generator, and the movement sensor is configured to detect changes to the spatial disposition of the targets by measuring changes to the electromagnetic field (e.g., using one or more electromagnetic sensors or the field generator itself) resulting from the movement. Alternatively or in combination, the electromagnetic targets can actively produce electromagnetic signals that are detected by the monitoring device (e.g., using one or more electromagnetic sensors or the field generator itself) and used to determine the changes to the spatial disposition of the targets. The spatial disposition of a target can be measured with respect to up to three degrees of freedom in position and three degrees of freedom in orientation, and with sufficient accuracy so as to enable the monitoring device to determine the corresponding movements of the patient's teeth. The determined movements can be compared to the planned movements for the teeth in order to evaluate the appliance performance.

Figure 10A:
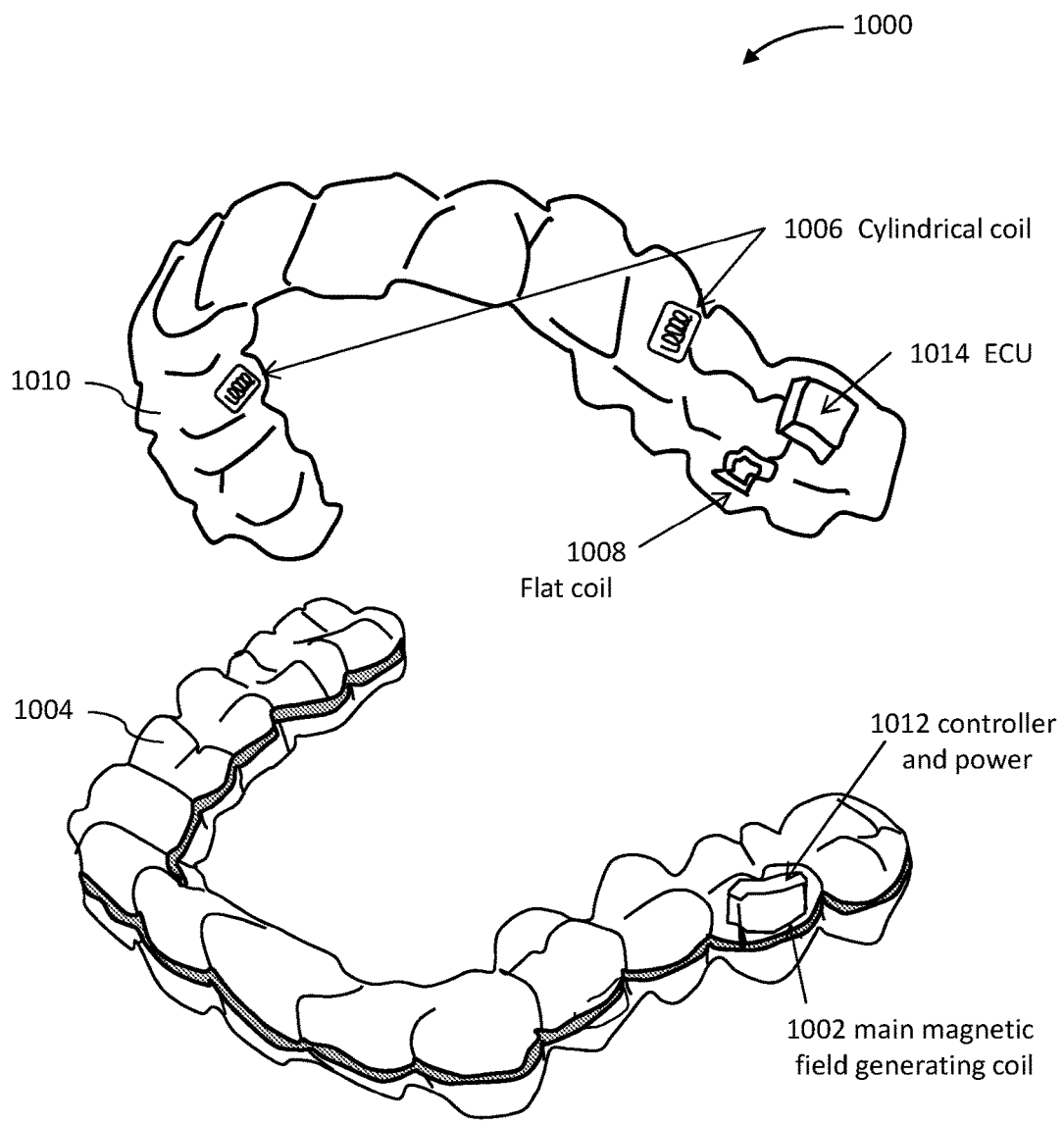
FIG. 10A illustrates a monitoring device for electromagnetic tooth tracking.

FIG. 10A illustrates a monitoring device 1000 for electromagnetic tooth tracking, in accordance with embodiments. The device 1000 includes an electromagnetic field generator 1002 (e.g., a coil) coupled to a first orthodontic appliance 1004 worn on the patient's jaw, and a plurality of electromagnetic targets (e.g., cylindrical coils 1006, flat coil 1008) coupled to a second orthodontic appliance 1010 worn on the opposing jaw. In alternative embodiments, some or all of the targets can also be coupled to the first appliance 1004. Optionally, the field generator 1002 and the targets can be located on both appliances 1004, 1010. The device 1000 can include a first controller subunit 1012 located on the first appliance 1004 and a second controller subunit 1014 located on the second appliance 1010. The first controller subunit 1012 and second controller subunit 1014 can each include a controller, power source, and/or any of the other monitoring device components described herein (e.g., with respect to FIG. 3A). The first controller subunit 1012 can be electrically coupled to and configured to control the operation of the field generator 1002, while the second controller subunit 1014 can be electrically coupled to and configured to control the operation of the electromagnetic targets. In some embodiments, when the first appliance 1004 and second appliance 1010 are worn by the patient, movements of the patient's teeth produce deflections in the second appliance 1010 which in turn cause changes in the spatial disposition of the electromagnetic targets that influence the characteristics (e.g., magnitude, direction) of the magnetic field produced by the field generator 1002. These changes can be detected by the field generator 1002 and analyzed by the monitoring device 1000 (e.g., by the first controller subunit 1012 and/or second controller subunit 1014) in order to determine the movements of the patient's teeth.

Alternatively or additionally, the electromagnetic target(s) may be positioned on one or more attachments that are coupled to individual teeth. Alternatively or additionally, one or more electromagnetic target(s) may be positioned directly on the tooth or teeth and may directly track movement.

Alternatively or in combination, a monitoring device can include one or more strain gauges (e.g., resistive or MEMS-based) to detect the stress and/or strain at one or more locations in the orthodontic appliance. In some embodiments, changes in tooth position cause corresponding changes in the stress and/or strain on the orthodontic appliance. Optionally, the amount of strain produced by changes in tooth position may fall in the linear behavior range of the appliance material. Accordingly, the monitoring device can process and analyze the stress and/or strain data in order to detect and track movements of the patient's teeth.

Alternatively or in combination, a monitoring device can include one or more electrical sensors (e.g., electrodes) to measure tooth surface charges. Alveolar bone remodeling during orthodontic tooth movement may be regulated by stress-induced bioelectric potentials on the tooth surface. For example, a force applied to the labial surface of the lower incisor can displace the tooth in its socket, deforming the alveolar bone convexly towards the root at the leading edge, and producing concavity towards the root at the trailing edge. In some embodiments, concave bone surfaces characterized by osteoblastic activity are electronegative, and convex bone surfaces characterized by osteoclastic activity are electropositive or electrically neutral. Accordingly, the monitoring device can measure the electrical charges on the tooth surface in order to determine the tooth movement rate and/or direction.

Alternatively or in combination, a monitoring device can include one or more conductivity sensors configured to measure the conductivity of fluids (e.g., saliva) in the surrounding environment. In some embodiments, bone remodeling during orthodontic tooth movement causes changes in saliva content, and these changes can be measured based on the ionic charge of the minerals in the saliva. Examples of minerals that may influence the conductivity of saliva include but are not limited to $NH_4^+$, $Ca^{2+}$, $PO_4^{3-}$, $HCO_3^-$, and $F^-$.

Figure 10B:
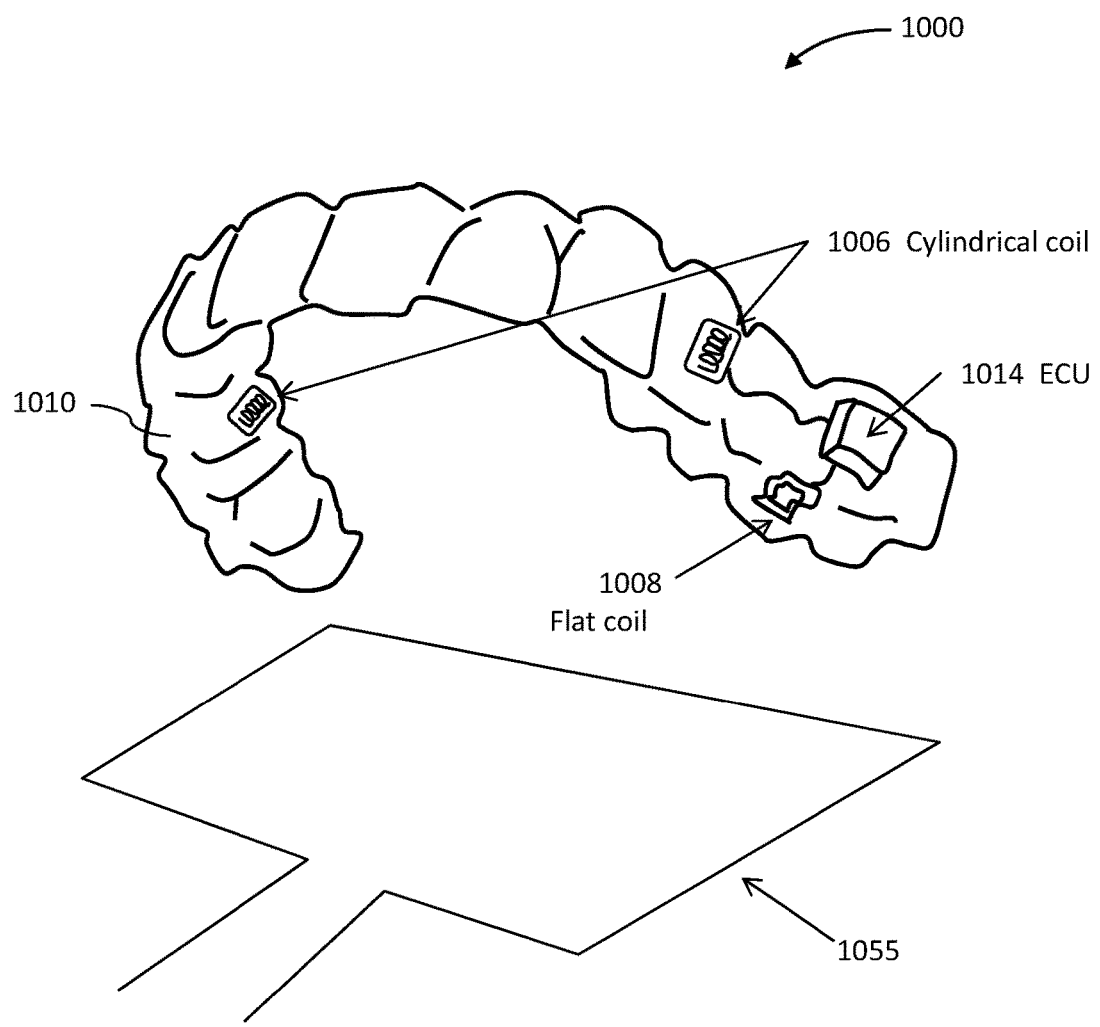
FIG. 10B illustrates an alternative to the monitoring device of FIG. 10A, in which a hand-held reader device may be used by a doctor or patient to read the position and/or orientation of the teeth.

As an alternative or additional means for determining the orientation of the teeth shown in FIG. 10A, in which a sensing coil ("main coil") is on the opposite arch, FIG. 10B illustrates an example in which a coil that may be used for sensing is on a hand-hold device 1055 that the doctor or patient can insert into the mouth to read the position and orientation of the teeth; the reader 1055 may then be removed. As mentioned, the reader may include one or more coils, and/or a field generator.

In general, the coils described herein may be passive (e.g., not requiring a battery or chip) or active (e.g., attached to a battery or other power supply). Passive coils may be charged via induction. Individual or multiple coils can be connected to a tag or data logger for logging data if needed.

In any of the variations described herein a 3D configuration of the capacitive sensing electrodes may be detected.

Figure 11:
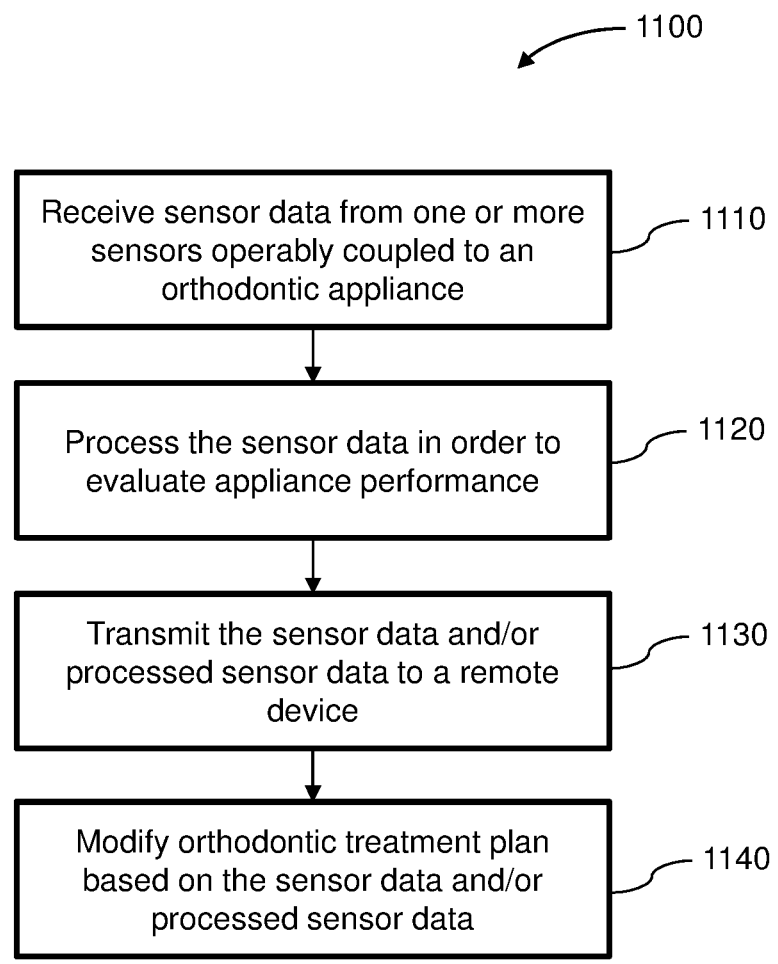
FIG. 11 illustrates a method for monitoring performance of an orthodontic appliance for repositioning a patient's teeth.
Figure 12A:
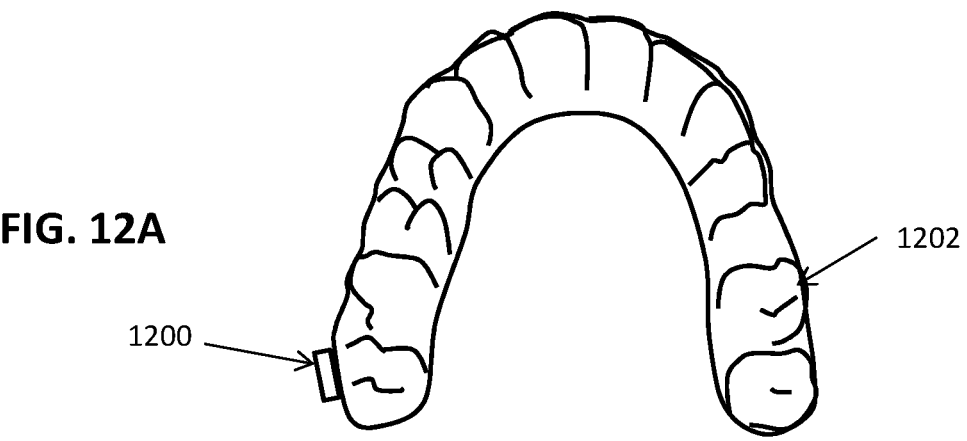
FIGS. 12A through 12D illustrate a method for fabricating an orthodontic appliance with an integrated monitoring device.
Figure 12B:
Figure 12C:
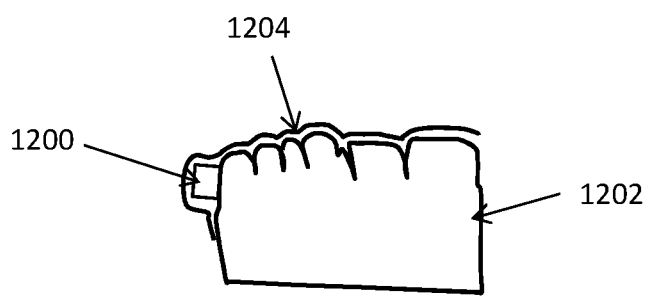
Figure 12D:
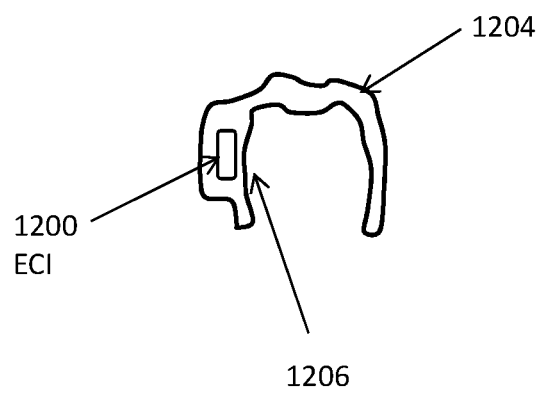

FIG. 11 illustrates a method 1100 for monitoring performance of an orthodontic appliance for repositioning a patient's teeth, in accordance with embodiments. The method 1100 can be performed using any embodiment of the systems and devices described herein. In some embodiments, some or all of the steps are performed using a processor of a monitoring device operably coupled to an orthodontic appliance. Alternatively or in combination, some or all of the steps can be performed by a processor of a device external to the patient's intraoral cavity, e.g., a separate computing device or system.

In step 1110, sensor data is received from one or more sensors operably coupled to an orthodontic appliance. The one or more sensors can include any of the sensor types described herein, including but not limited to: touch or tactile sensors (e.g., capacitive, resistive), proximity sensors, movement sensors (e.g., electromagnetic field sensors), force sensors (e.g., force-sensitive films), pressure sensors (e.g., pressure-sensitive films), strain gauges (e.g., resistive- or MEMS-based), electrical sensors, or combinations thereof.

The orthodontic appliance can be worn by the patient as part of a treatment plan for incrementally repositioning the patient's teeth, as described herein. In some embodiments, the orthodontic appliance includes teeth receiving cavities shaped to reposition one or more teeth according to a prescribed treatment plan, and the sensor(s) can be physically integrated with (e.g., coupled to, embedded in, formed with, etc.) the orthodontic appliance at locations adjacent to or near the teeth to be repositioned. The sensor data can be related to the repositioning of the patient's teeth by the orthodontic appliance, in accordance with the embodiments described herein. For example, the sensor data can provide information regarding movements (e.g., rotational, translational) of one or more teeth. As another example, the sensor data can provide information regarding the interaction between the orthodontic appliance and the patient's teeth or attachments mounted thereto, such as the force and/or pressure applied by the appliance to the teeth and/or attachments.

In some embodiments, the sensor data is generated and logged continuously. Alternatively, in order to reduce power consumption, the sensor data can be obtained at predetermined time intervals, such as once every 15 minutes, 30 minutes, 1 hour, 2 hours, 5 hours, 12 hours, or 24 hours. The timing for sensor data collection may vary based on the expected tooth movements to be produced by the orthodontic appliance. For example, in some embodiments, tooth tipping is expected to occur relatively rapidly after the patient starts wearing the appliance, such that monitoring for tooth tipping is performed during the first 12 hours of appliance usage.

In step 1120, the sensor data is processed in order to evaluate the performance of the orthodontic appliance in repositioning the patient's teeth. For example, the sensor data can include measurements of the force and/or pressure applied to the teeth by the appliance, and the processing step can involve determining whether the force and/or pressure measurements fall within a targeted range of values, e.g., for repositioning the teeth. Alternatively or in combination, the sensor data can include measurement of changes in the spatial disposition (e.g., position and/or orientation) of one or more teeth, and the processing step can involve determining whether the changes in spatial disposition correspond to planned movements for the patient's teeth. Optionally, the processing step can involve associating the sensor data with a timestamp representing when the data was obtained such that appliance performance information can be measured over time.

The processed sensor data can include appliance performance information, e.g., whether the force(s), pressure(s), and/or tooth movement(s) produced by the appliance correlate well with the expected values for the planned orthodontic treatment. The expected values for a planned treatment may be determined by computer simulation. For example, an orthodontic appliance can be considered to be performing satisfactorily if: (1) the measured force and/or pressure values lie within the expected range for those values, or is within 70% of a targeted value; (2) the pattern of force and/or pressure application on the teeth matches, or is similar to, the planned pattern for force and/or pressure application; (3) the amount of tooth movement achieved is within 70% of the planned movement; (4) the direction of tooth movement matches, or is similar to, the planned direction of tooth movement; or combinations thereof. An orthodontic appliance can be considered to be performing unsatisfactorily if: (1) the measured force and/or pressure values lie outside the expected range for those values or is more than 30% away from a targeted value; (2) the pattern of force and/or pressure application on the teeth differs from the planned pattern for force and/or pressure application; (3) the amount of tooth movement achieved is more than 30% away from the planned movement; (4) the direction of tooth movement is different to the planned direction of tooth movement; or combinations thereof.

In step 1130, the sensor data generated in step 1110 and/or the processed sensor data generated in step 1120 are optionally transmitted to a remote device. The remote device can be a mobile device (e.g., smartphone), personal computer, laptop, tablet, wearable device, cloud computing server, or the like. Step 1130 can be performed using wireless or wired communication methods, as desired. Step 1130 can be performed automatically (e.g., at predetermined time intervals) or in response to instructions received from the remote device (e.g., a command to transmit the sensor data and/or appliance usage).

In step 1140, the orthodontic treatment plan prescribed to the patient is optionally modified based on the sensor data generated in step 1110 and/or the processed sensor data generated in step 1120. The modification step can be performed by a processor external to the patient's intraoral cavity, such as a remote device as in step 1130. Modifying the treatment plan can involve modifying a planned intermediate or final arrangement of the patient's teeth, modifying the teeth receiving cavity geometries of an orthodontic appliance corresponding to a planned intermediate or final tooth arrangement, modifying the timing for wearing one or more appliances, modifying the order for wearing a series of appliances, or a combination thereof. For example, if the appliance performance information indicates that the tooth repositioning achieved by the orthodontic appliance is not satisfactory and the teeth are off-track, the treatment plan can be modified in order to move the patient's teeth back on track (e.g., mid-course correction). As another example, if the appliance performance information indicates that the appliance is not producing the desired force and/or pressure pattern on the teeth, the geometries of subsequent appliances can be adjusted accordingly to provide more accurate force and/or pressure application. By using the appliance performance information as feedback, the systems, methods, and devices of the present disclosure allow for adaptive, closed-loop orthodontic treatment based on the actual response of the patient's teeth to treatment.

The monitoring devices described herein can be physically integrated into an orthodontic appliance in a variety of ways. In some embodiments, the monitoring device is integrated into the appliance during or after fabrication of the appliance. For example, the monitoring device can be attached to an appliance using adhesives, fasteners, a latching mechanism, or a combination thereof after the appliance has been fabricated. Optionally, the appliance can be formed with complementary features or structures (e.g., recesses, receptacles, guides, apertures, etc.) shaped to receive and accommodate the monitoring device or components thereof.

In some embodiments, a monitoring device is coupled to the appliance as a prefabricated unit during or after fabrication of the appliance, such as by being inserted and sealed into a receptacle in the appliance, attached to an appliance (e.g., by a latching mechanism, adhesive, fastener). Alternatively, the monitoring device can be assembled in situ on the appliance during or after appliance fabrication. For instance, in embodiments where the appliance is manufactured by direct fabrication (e.g., 3D printing), the monitoring device can be printed simultaneously with the appliance, inserted into the appliance during fabrication, or after assembled the appliance has been fabricated. Optionally, some of the monitoring device components may be prefabricated and other components may be assembled in situ. It shall be appreciated that the various fabrication methods described herein can be combined in various ways in order to produce an appliance with integrated monitoring device components.

FIGS. 12A through 12D illustrate a method for fabricating an orthodontic appliance with an integrated monitoring device, in accordance with embodiments. The method can be applied to any embodiment of the monitoring devices and appliances described herein, and can be used in combination with any of the other fabrication methods described herein. In a first step (FIGS. 12A (top view) and 12B (side view)), a prefabricated monitoring device 1200 is coupled to a positive model 1202 of a patient's dentition. The monitoring device 1200 can be attached using an adhesive and/or a mechanical fastener, for example. Optionally, the monitoring device 1200 can be hermetically sealed prior to being attached to the model 1202. In a second step (FIG. 12C), a material is formed (e.g., thermoformed) over the monitoring device 1200 and model 1202 so as to produce an appliance shell 1204. In a third step (FIG. 12D), the mold 1202 is removed, resulting in an appliance shell 1204 with an embedded monitoring device 1200. Optionally, the monitoring device 1200 can be encapsulated using a biocompatible adhesive 1206 (e.g., a UV-curable glue), a layer of material, or other sealing element.

Figure 13A:
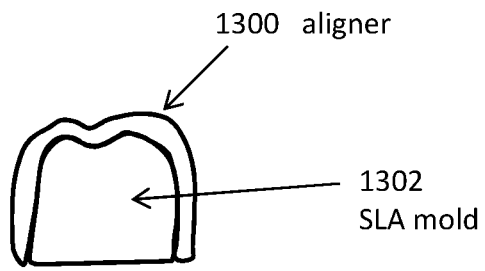
FIGS. 13A through 13C illustrate a method for fabricating an orthodontic appliance with an integrated monitoring device.
Figure 13B:
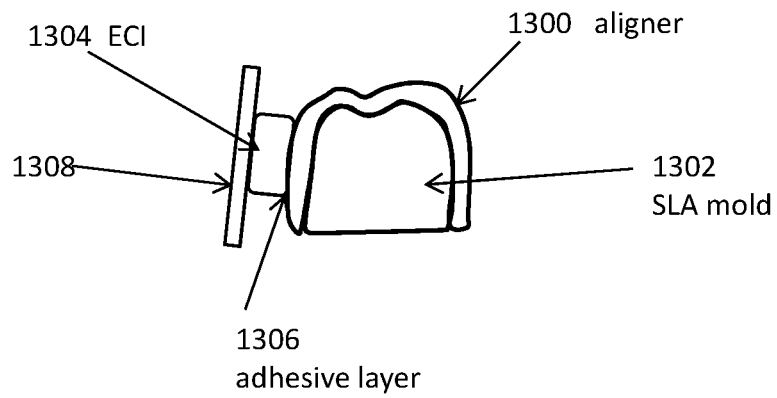
Figure 13C:
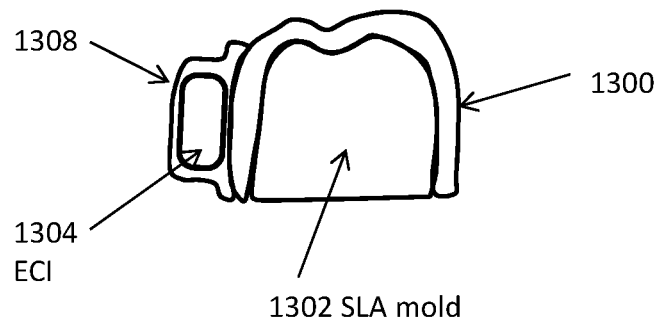

FIGS. 13A through 13C illustrate a method for fabricating an orthodontic appliance with an integrated monitoring device, in accordance with embodiments. The method can be applied to any embodiment of the monitoring devices and appliances described herein, and can be used in combination with any of the other fabrication methods described herein. In a first step (FIG. 13A), an appliance 1300 is formed (e.g., thermoformed) over a positive model 1302 of a patient's dentition. In a second step (FIG. 13B), a prefabricated monitoring device 1304 is attached to the appliance 1300, e.g., using an adhesive layer 1306 and/or fastener, and a thermoplastic material 1308 is attached to the outer surface of the monitoring device 1304. In a third step (FIG. 13C), the thermoplastic material 1308 is thermoformed so as to form a cover encapsulating the monitoring device 1304 into the appliance 1300. The positive model 1302 can be removed e.g., before or after the third step.

Alternatively or in combination, the method can involve forming a positive geometry corresponding to the geometry of the monitoring device 1304 on the positive model 1302 (e.g., by 3D printing, CNC milling, etc.), such that the appliance 1300 is thermoformed with a receptacle for the monitoring device 1304. The monitoring device 1304 can then be placed and sealed into the receptacle.

Alternatively or in combination, an orthodontic appliance with an integrated monitoring device can be produced by fabricating the appliance (e.g., by indirect or direct fabrication), then attaching a prefabricated monitoring device to the fabricated appliance, e.g., using adhesives, fasteners, a latching mechanism, etc. Optionally, the monitoring device can be hermetically sealed (e.g., by molding) before being attached to the appliance.

Alternatively or in combination, an orthodontic appliance with an integrated monitoring device can be fabricated by coupling flexible and/or printed components of a monitoring device onto the appliance during or after forming the appliance. The components can be coupled in various ways, such as thermoforming, laminating, adhesives, coating, and so on.

Alternatively or in combination, an orthodontic appliance with an integrated monitoring device can be fabricated by 3D printing a base for the monitoring device, then building up the electronic components for the monitoring device onto the base. In some embodiments, the base is shaped to conform to the geometry of the tooth receiving cavity and/or target tooth where the monitoring device will be located. The 3D printed portions of the monitoring device can be shaped to lie flush with the surface of the appliance to facilitate integration of the monitoring device with the appliance.

Alternatively or in combination, an orthodontic appliance with an integrated monitoring device can be fabricated by etching the surface of the appliance (e.g., using a masking process) and then depositing conductive inks, stretchable materials, etc. onto the etched portions to build up the electronic components of the monitoring device (e.g., wires, connections, electrodes, etc.) on the appliance.

Figure 14:
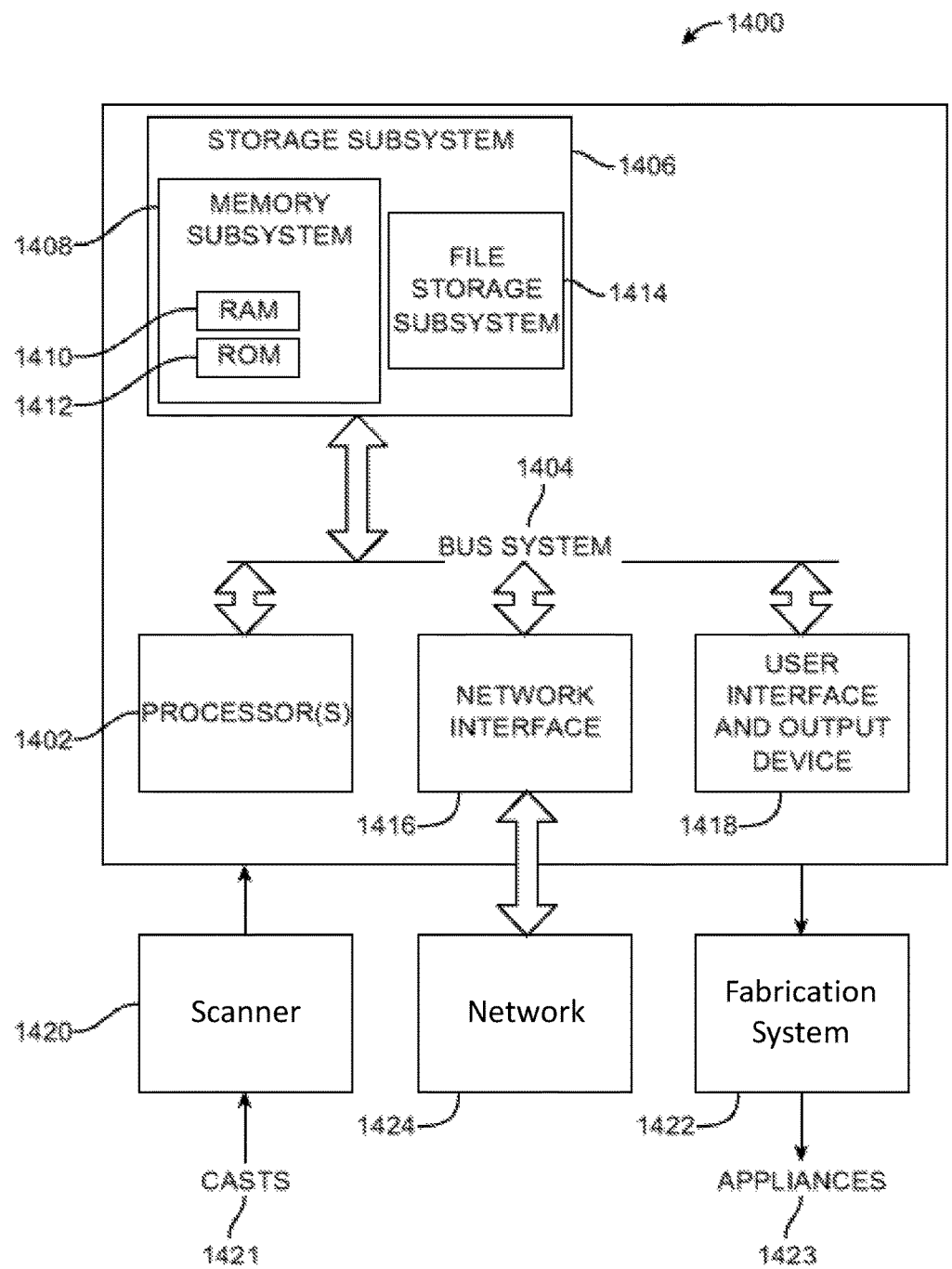
FIG. 14 is a simplified block diagram of a data processing system.

FIG. 14 is a simplified block diagram of a data processing system 1400 that may be used in executing methods and processes described herein. The data processing system 1400 typically includes at least one processor 1402 that communicates with one or more peripheral devices via bus subsystem 1404. These peripheral devices typically include a storage subsystem 1406 (memory subsystem 1408 and file storage subsystem 1414), a set of user interface input and output devices 1418, and an interface to outside networks 1416. This interface is shown schematically as "Network Interface" block 1416, and is coupled to corresponding interface devices in other data processing systems via communication network interface 1424. Data processing system 1400 can include, for example, one or more computers, such as a personal computer, workstation, mainframe, laptop, and the like.

The user interface input devices 1418 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1406 maintains the basic required programming, including computer readable media having instructions (e.g., operating instructions, etc.), and data constructs. The program modules discussed herein are typically stored in storage subsystem 1406. Storage subsystem 1406 typically includes memory subsystem 1408 and file storage subsystem 1414. Memory subsystem 1408 typically includes a number of memories (e.g., RAM 1410, ROM 1412, etc.) including computer readable memory for storage of fixed instructions, instructions and data during program execution, basic input/output system, etc. File storage subsystem 1414 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1420 includes any means for obtaining a digital representation (e.g., images, surface topography data, etc.) of a patient's teeth (e.g., by scanning physical models of the teeth such as casts 1421, by scanning impressions taken of the teeth, or by directly scanning the intraoral cavity), which can be obtained either from the patient or from treating professional, such as an orthodontist, and includes means of providing the digital representation to data processing system 1400 for further processing. Scanner 1420 may be located at a location remote with respect to other components of the system and can communicate image data and/or information to data processing system 1400, for example, via a network interface 1424. Fabrication system 1422 fabricates appliances 1423 based on a treatment plan, including data set information received from data processing system 1400. Fabrication system 1422 can, for example, be located at a remote location and receive data set information from data processing system 1400 via network interface 1424.

Any of the apparatuses and methods described herein may include a plurality of sensors, including force sensors, arranged as an array over each tooth; multiple teeth may each be covered with an array of sensors. These sensors may be used to determine a force or pressure pattern across one or more of the subject's teeth. The pattern of force or pressure may be correlated, for example, with a scan of subject's teeth, as mentioned in reference to FIG. 3B and FIG. 14, above. Thus, the sensor information may be combined with digital scan information of the morphology of the patient's teeth. The spatial distribution pattern of force/pressure on one or more of the subject's teeth may be used to determine the orientation of the forces being applied by a dental appliance with respect to the tooth, and may be used to determine a prediction for tooth movement based on the current and/or proposed forces applied to the teeth.

Any number of sensors may be arranged over each tooth. For example, each tooth may be covered (e.g., on the aligner, on a dental attachment configured to couple with a tooth, or directly on the tooth and configured to couple with an orthodontic appliance) by two, three, four, or more (e.g., n) force sensors. In some variations the sensors are otherwise similar or identical, but are arranged in an array (e.g., an l by w array of n sensors). This is illustrated for example, in FIG.

Figure 15A:
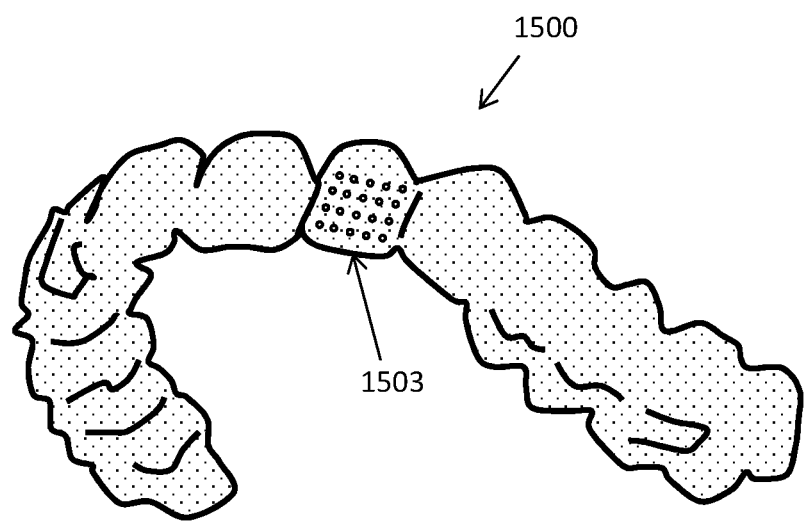
FIG. 15A is an example of an aligner having an array of multiple force and/or pressure sensors corresponding to each tooth to provide a within-tooth pattern of force and/or pressure that may be used by the apparatuses described herein to determine an accurate estimation of tooth movement and therefore modify treatment (adaptive treatment). The intraoral appliance shown in FIG. 15A is an aligner, though any appliance may be used, and although only a single tooth is shown with an array, multiple arrays (on multiple teeth) may be included, similar to the example shown in FIGS. 8B-8C, e.g., capacitive touch sensor array.

15A, showing a dental appliance 1501 (configured as an aligner) to be worn on a subject's teeth. The appliance is configured as an aligner having a body with a plurality of teeth receiving cavities shaped to receive the patient's teeth and to apply force to reposition the patient's teeth from an initial arrangement towards a target arrangement. In FIG. 15A, an array of sensors is shown on just a single tooth 1503 corresponding to a portion of the aligner. In some variations it may be beneficial to include just a single tooth or a few teeth in the aligner, including a tooth that is particularly targeted for movement. Alternatively, any number (including all) of the teeth to be held in the apparatus may be monitored using arrays of force sensors, as shown in FIG. 15B.

Figure 15B:
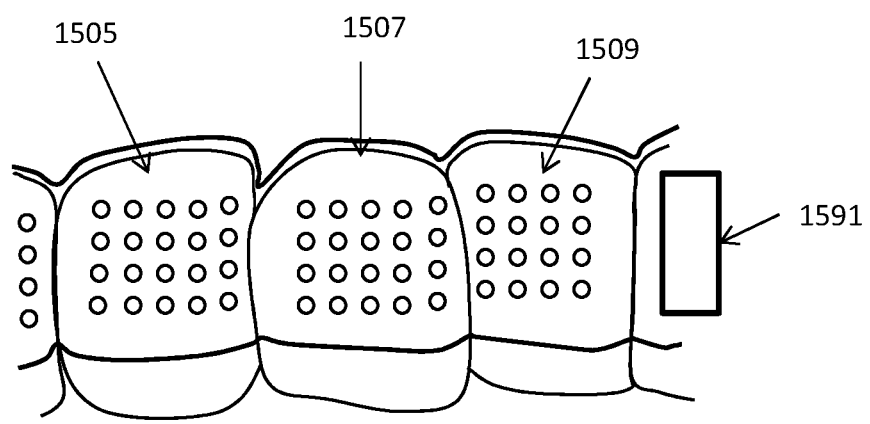
FIG. 15B shows a portion of an aligner with an array of force sensors similar to that shown in FIG. 15A, worn on a subject's teeth; in this example, multiple arrays (at least one array of n sensors per tooth) are shown.

FIG. 15B shows an enlarged view of a portion of an orthodontic appliance such as the one shown in FIG. 15A, including a plurality of arrays 1505, 1507, 1509 of force sensors configured to be arranged across the surface(s) of each tooth. In this example, the aligner also includes a processor 1591 that receives input from the plurality of sensors, and may analyze, store and/or transmit the signals from the sensors. The processor may include a memory, a communications circuitry (e.g., wireless communications circuitry, etc.), a power source (e.g., battery), etc. In FIGS. 15A and 15B the array of sensors are shown as regularly-spaced force sensors; alternatively or additionally, the force sensors may be differentially spaced, and may be spaced on the front (buccal), back (lingual) or sides of the teeth, e.g., coupled to the appliance. Each sensor may be in electrical connection with the processor(s) on the appliance and/or held on attachments on the tooth or teeth.

Figure 16A:
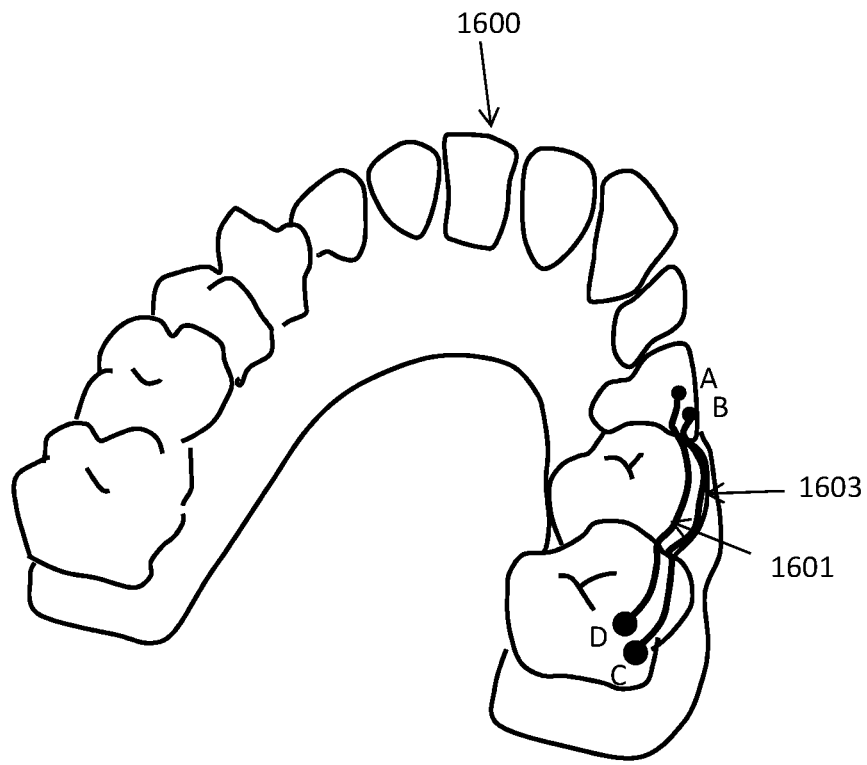
FIG. 16A is an example of an apparatus including an electrical trace that is bonded directly to the subject's teeth and configured to interact with electrical circuitry and/or power on a wearable orthodontic piece (e.g., aligner). In this example, wearing the aligner properly on the teeth completes a circuit in the aligner that may accurately trace compliance and/or may activate a sensor (e.g., biosensor).
Figure 16B:
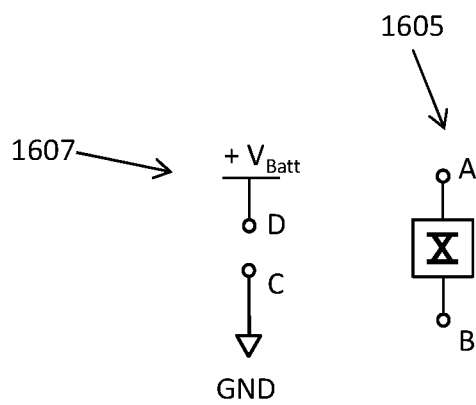
FIG. 16B illustrates the open circuit between the appliance (e.g., aligner, on left) and conductive traces on teeth when the appliance is not worn on the teeth or is improperly worn.
Figure 16C:
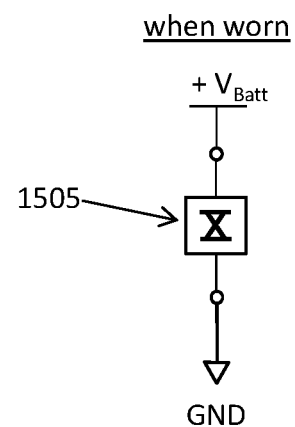
FIG. 16C shows the closed circuit, when the appliance is worn so that the nodes on the teeth are coupled to the nodes on the appliance.

As mentioned, any of the apparatuses described herein may include a portion of the sensor, sensor processor, power supply, memory, etc., on the appliance (e.g., aligner, etc.) and/or directly connected to the teeth via an attachment or other tooth-coupling technique (e.g., bonding, etc.). The component on the tooth/teeth may therefore integrate with the portion on the orthodontic appliance(s) worn by the patient. For example, FIGS. 16A-16C illustrate an example of an apparatus including at least a portion (shown as traces 1601, 1603) that is bonded directly to the subject's teeth 1600, which integrates with a portion on an orthodontic appliance (e.g., shown as an aligner in this example). In FIG. 16A, the apparatus includes a trace or traces (e.g., stretchable conductive traces 1601, 1603) that are directly attached to the teeth. In this example, the traces connect nodes A and B to the power supply nodes C and D, which may be on an aligner (e.g., aligner 1605). This configuration may eliminate leakage current from the battery to the components (X) when the aligner is not in the mouth. In one example, the components generically referred to as "X" in FIG. 16A-16C could include one or more sensors, electronics (e.g., controller, memory, power, wireless communication, etc.). For example, the apparatus may be configured to emit a BLE signal every few minutes (e.g., every minute, 2 minutes, 3 minutes, 5 minutes, 10 minutes, 15 minutes, etc., or variable intervals/times) when the aligner is worn. A receiver (e.g., smartphone and/or dedicated receiver) could track the BLE pulses and monitor when the appliance is in the mouth.

In FIG. 16A, the traces 1603, 1301 shown on the teeth 1600 can be used to connect to rigid components on the aligner. Different electronic circuits may be used when the aligner is in the mouth and for when the aligner is outside of the mouth. For example, traces such as those shown above can be used as performance measures for aligners or tooth movements. Nodes 1607 can be placed to be at known positions on the aligner and compared with nodes positions on teeth. In some variations a printed potentiometer may be applied to the teeth. As shown in FIG. 16B, before the aligner is worn, the contacts (A, B) or nodes 1607 are not connected, to the power (on left, nodes D and C), which may be on the aligner. When the aligner is worn (shown in FIG. 16C), the circuit is completed, as nodes A and D connect and nodes B and C connect by the conductive trace on the teeth. At a minimum, this completed circuit may be used to indicate compliance, as it will only complete the circuit when the appliance is worn, and worn correctly. Alternatively, additional sensor(s), including one or more sensor, may also be connected to the traces on the subject's teeth (either on the tooth/teeth, or on the aligner) and activated when the appliance is worn. In some variations, the use of conductive traces on the teeth that may interface with contacts on an aligner may also be used to check the fit of an aligner.

In some variations the traces, such as those shown in FIGS. 16A-16C may be magnetic, which may allow self-healing of the traces, or may also be used for other purposes, including detection (e.g., via a reed switch or hall-effect sensor, etc.) including detection of teeth.

Distributed Monitoring/Sensing Apparatuses

As already mentioned above, and shown in FIGS. 7D-7G, 9A-9B and 16A-16C, any of these methods and apparatuses described herein may be distributed apparatuses in which the orthodontic appliance including multiple parts (e.g., an aligner body and an attachment) and the sensor sub-system is distributed between the parts.

Figure 17A:
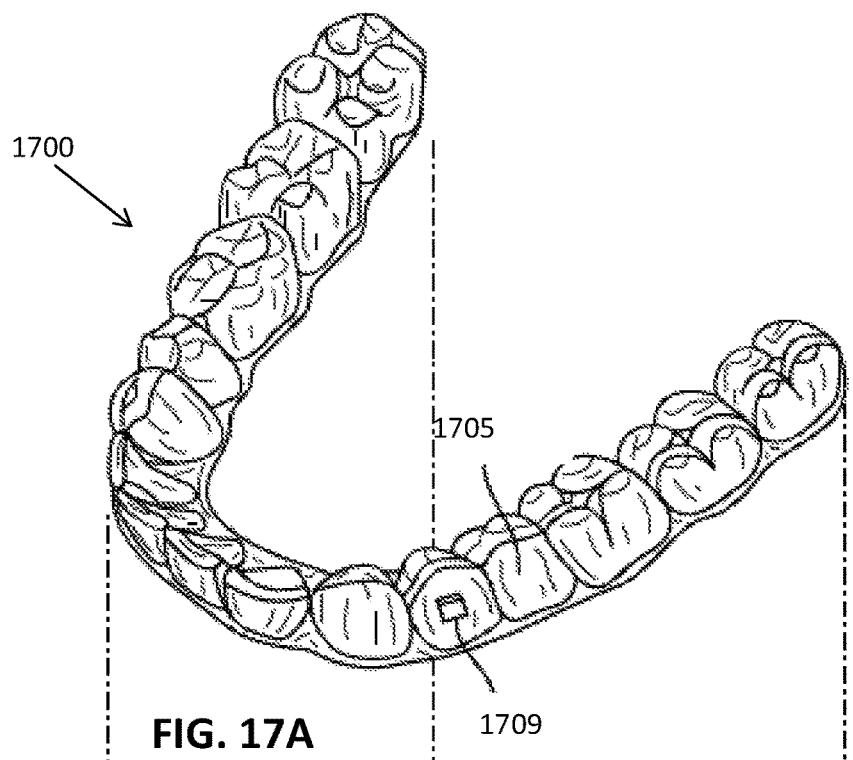
FIG. 17A shows an aligner including a plurality of engagement sites.
Figure 17B:
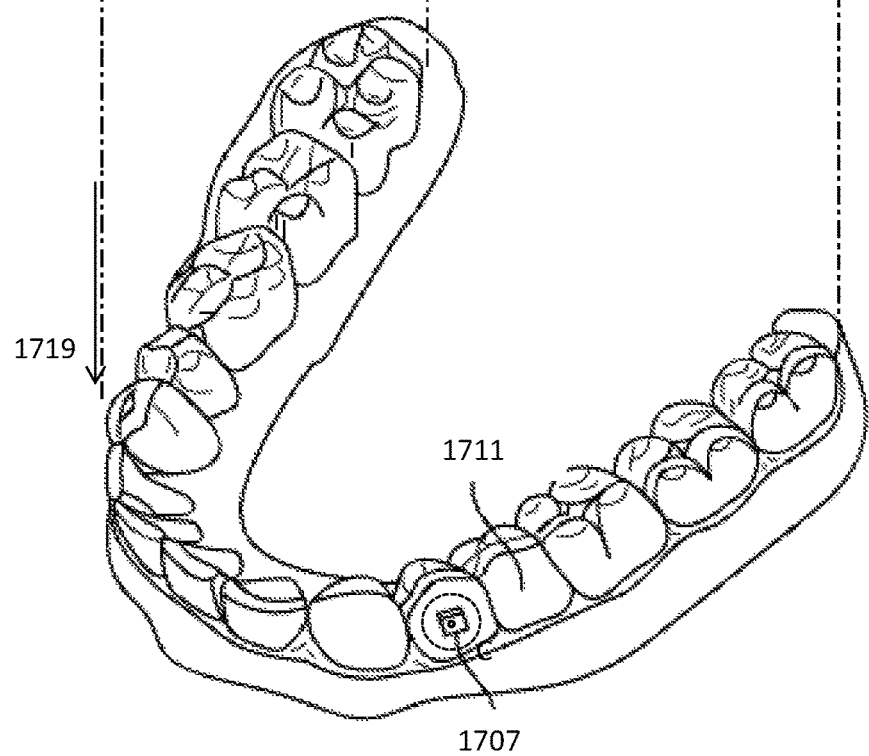
FIG. 17B shows a patient's teeth and an attachment configured to engage with the aligner in FIG. 17A. A sensor subsystem may be distributed between the aligner and one or more of these attachments (which may also be referred to herein as attachments) securing the aligner to the teeth; and electrical contact may be made between the attachment and the aligner and the sensor may electrically communicate (e.g., transmit sensor data) through the electrical contact to a memory, processor, etc. For example, in FIG. 17C, showing an enlarged view of an attachment site, a sensor is integrated into the attachment, which also includes and electrical contact.

As illustrated in FIG. 17A-17B, the apparatus may include an aligner body 1700 having a plurality of teeth receiving cavities 1705 shaped to reposition the patient's teeth from an initial arrangement towards a target arrangement. The aligner body may include one (or, preferably, more than one) engagement sites 1709 for attaching to an attachment 1707 (shown in FIG. 17B). As show, the attachment may be bonded to the patient's tooth/teeth and may engage with the engagement site on the aligner body to receive force and/or to secure the aligner body to the patient's teeth (arrows 1719).

In general, any portion of the sensor sub-assembly of the apparatus may be on the attachment(s) and the aligner, and may be distributed between them. This may allow the portion on the aligner, which is removed regularly, to be recharged, download/uploaded, etc., while leaving other portions attached to the teeth. For example, the processor, memory and/or battery may be on the aligner, and the sensor may be on the attachment. Alternatively, the processor, memory and/or battery may be on the attachment and the sensor may be on the aligner.

Figure 17C:
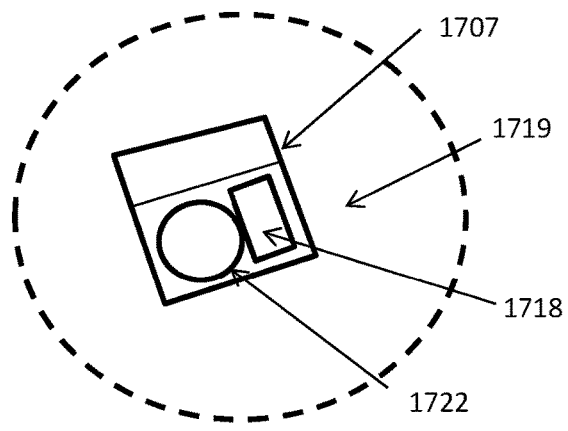
FIG. 17D shows the connection between the attachment and an engagement site of an aligner, which also includes an electrical contact.
FIG. 17E shows an alternative configuration, in which a portion of the sensor subsystem (e.g., the processor and/or battery) but not the sensor is on the attachment. This portion may electrically connect with the processor through the electrical contacts between the attachment and the engagement site on the aligner, as shown in FIG. 17F.
Figure 17D:
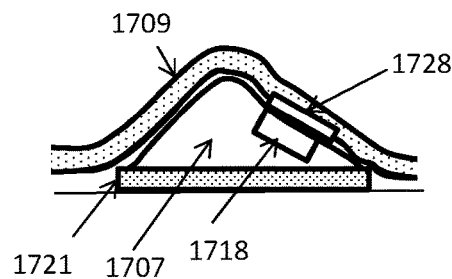

For example, in FIGS. 7C and 17D, a sensor is connected to the attachment. FIG. 17C shows an example of a sensor 1722 coupled to the attachment 1707 (e.g., any appropriate sensor configured to generate sensor data). The sensor 1722 in this example is embedded in or attached to the attachment 1707, and the attachment 1707 is bonded to (or configured to bond to) the tooth 1719. For example, dental cement or adhesive 1721 may secure the attachment to the tooth 1719. The attachment 1707 may include a surface that projects from the tooth and to which the engagement site on the aligner body engages. In some variations the sensor is part of the surface between the attachment and the engagement site.

The attachment may also include an electrical contact 1718 for forming an electrical connection between with a complimentary electrical contact 1728 on the aligner body. In FIG. 17C, a first electrical contact 1718 is included on the attachment (attachment 1707) over or in electrical contact with the sensor 1722. The first electrical contact 1718 on the attachment 1707 may make and electrical connection with a second electrical contact 1728 on the aligner body when the aligner is retained by the attachment, as shown in FIG. 17D. The first electrical contact 1718 and the second electrical contact 1728 may form an electrical connection, and sensor data may be transferred through this connection when the attachment 1707 is engaged with the engagement site on the aligner 1700.

Figure 17E:
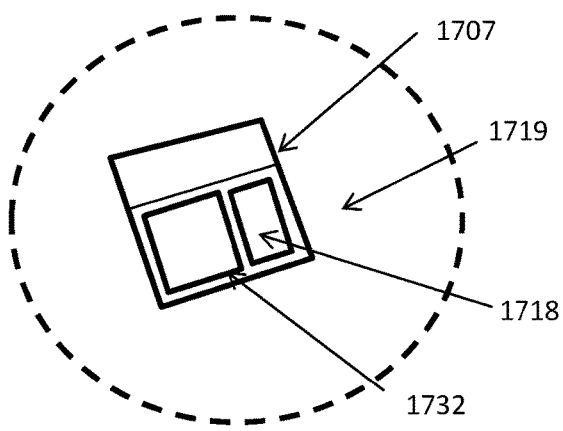
Figure 17F:
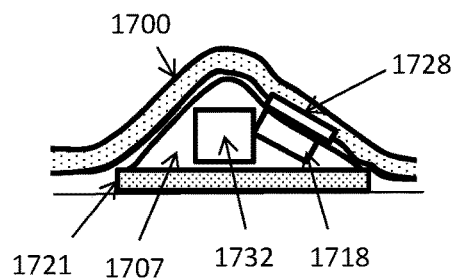

Alternatively, the sensor may be on the aligner, and other components (e.g., the battery, the processor, and/or a memory) may be on the attachment. For example, in FIG. 17E, the processor 1732 and/or battery are shown in the attachment 1707. In this example, the sensor may be in electrical communication with the processor and/or battery through the electrical connection formed by the first electrical contact 1718 on the attachment and the second electrical contact 1728 on the aligner body when the attachment is engaged with the engagement site. Thus, in FIG. 17E, the sensor is not on the attachment 1707, but at least a portion of the processor 1732 is on the attachment (e.g., the processor, and/or memory, timer, etc.) and/or battery is a part of the attachment and may connect to the other portions of the sensory subsystem (including the sensor) through an electrical connector 1718 that makes electrical contact with another electrical connector 1728 on the aligner when the aligner is worn on the teeth and over the attachment, as shown in FIG. 17F.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthodontic apparatus for repositioning a patient's teeth and for sensing one or more characteristics from the patient's oral cavity, the apparatus comprising:
    an aligner body comprising a plurality of teeth receiving cavities shaped to reposition the patient's teeth from an initial arrangement towards a target arrangement, the aligner body having an engagement site;
    an attachment configured to be bonded to the patient's teeth and to engage with the engagement site on the aligner body;
    a sensor configured to generate sensor data;
    a processor configured to receive the sensor data from the sensor and do one or more of: store, analyze and transmit the received sensor data; and
    a first electrical contact on the attachment and a second electrical contact on the aligner body, wherein the first electrical contact and the second electrical contact form an electrical connection when the attachment is engaged with the engagement site;
    wherein the sensor is on either the attachment or the aligner and wherein the sensor is in electrical communication with the processor through the electrical connection formed by the first electrical contact and the second electrical contact when the attachment is engaged with the engagement site.

2. The apparatus of claim 1, wherein the sensor is on the attachment and the processor is on the aligner body.

3. The apparatus of claim 1, wherein the processor is on the attachment and the sensor is on the aligner body.

4. The apparatus of claim 1, further comprising a power source on the aligner.

5. The apparatus of claim 1, further comprising a power source on the attachment.

6. The apparatus of claim 1, wherein the processor comprises one or more of: a memory, a wireless communications circuit, and a timer.

7. The apparatus of claim 1, wherein the sensor comprises a force or pressure sensor configured to measure force or pressure applied to one or more teeth by the orthodontic appliance.

8. The apparatus of claim 1, wherein the sensor comprises a force- or pressure-sensitive film, a resistive film, a capacitive film, or a piezoelectric tactile sensor.

9. The apparatus of claim 1, wherein the sensor comprises an electromagnetic target that is configured to generate movement sensor data indicating one or more of: a position of the patient's tooth and an orientation of the patient's tooth; further wherein the aligner body comprises an electromagnetic field generator.

10. The apparatus of claim 1, wherein the engagement site comprise an opening or concavity formed through the aligner body.

11. The apparatus of claim 1, wherein the engagement site is located on one or more of a lingual side of the aligner body or a buccal side of the aligner body.

12. The apparatus of claim 1, further comprising a plurality of additional engagement sites on the aligner body and plurality of additional attachments configured to be bonded to the patient's teeth and to engage with the additional engagement sites.

13. The apparatus of claim 1, wherein the processor is configured to evaluate a performance of the orthodontic appliance by using the sensor data to determine one or more of: an amount of force or pressure applied to the patient's teeth, a distribution of force or pressure on the patient's teeth, an amount of movement of the patient's teeth, or a movement rate of the patient's teeth.

14. The apparatus of claim 1, wherein the processor is configured to evaluate a performance of the orthodontic appliance by determining whether an amount of force or pressure applied to the patient's teeth by the orthodontic appliance is within a targeted range.

15. An orthodontic apparatus for repositioning a patient's teeth and for sensing one or more characteristics from the patient's oral cavity, the apparatus comprising:
    an aligner body comprising a plurality of teeth receiving cavities shaped to reposition the patient's teeth from an initial arrangement towards a target arrangement, the aligner body having an engagement site;
an attachment configured to be bonded to the patient's teeth and to engage with the engagement site on the aligner body;
a sensor on the attachment configured to generate sensor data;
a processor on the aligner configured to receive the sensor data from the sensor and do one or more of: store, analyze and transmit the received sensor data; and
a first electrical contact on the attachment and a second electrical contact on the aligner body, wherein the first electrical contact and the second electrical contact form an electrical connection when the attachment is engaged with the engagement site;
wherein the sensor is in electrical communication with the processor through the electrical connection formed by the first electrical contact and the second electrical contact when the attachment is engaged with the engagement site.

16. An orthodontic apparatus for repositioning a patient's teeth and tracking tooth movement, the apparatus comprising: an aligner body comprising a plurality of teeth receiving cavities shaped to reposition the patient's teeth from an initial arrangement towards a target arrangement; a plurality of movement sensors coupled to the aligner body or configured to couple with the aligner body, wherein each movement sensor is configured to generate movement sensor data indicating one or more of: a position of the patient's tooth and an orientation of the patient's tooth; and a processor configured to receive and store the movement sensor data and to determine tooth movement from the movement sensor data, wherein at least some of the movement sensors in the plurality of movement sensors are on attachments configured to be bonded to the patient's teeth and couple the aligner body to the patient's teeth.

17. The apparatus of claim 16, wherein the movement sensor data generated by each of the plurality of movement sensors indicates one or more of: two or more spatial positions of the patient's tooth and two or more angular positions of the patient's tooth.

18. The apparatus of claim 16, wherein the processor is configured to repeatedly receive and store the movement sensor data at an interval of between 1 hour and 2 weeks.

19. The apparatus of claim 16, further comprising a plurality of force sensors coupled to the aligner body or on attachments configured to couple the aligner body to the patient's teeth, and configured to generate force sensor data indicating one or more of: an amount of force applied to the patient's teeth and a direction of force applied to the patient's teeth, further wherein the processor is configured to receive and store the movement sensor data and the force sensor data.

20. The apparatus of claim 16, wherein each movement sensor of the plurality of movement sensors comprises an electromagnetic target that is configured to generate the movement sensor data.

21. The apparatus of claim 20, wherein each movement sensor of the plurality of movement sensors comprises a magnet, a flat coil or a cylindrical coil.

22. The apparatus of claim 20, further comprising an electromagnetic field generator coupled to the aligner body.

23. The apparatus of claim 16, wherein the movement sensor is configured to measure the position of the one or more teeth by measuring changes to an applied electromagnetic field.

24. The apparatus of claim 16, wherein the processor is configured to track movement of the patient's teeth relative to each other based on the movement sensor data.

25. The apparatus of claim 16, further comprising a power source and a wireless communication circuit coupled to the processor and configured to wirelessly transmit the movement sensor data.

26. The apparatus of claim 16, further comprising a second aligner body comprising a plurality of teeth receiving cavities.

27. The apparatus of claim 16, wherein at least some of the movement sensors in the plurality of movement sensors are coupled to the aligner body.

* * * * *